(12) United States Patent
Harb et al.

(10) Patent No.: US 10,345,235 B2
(45) Date of Patent: Jul. 9, 2019

(54) OPTICAL SIGNAL PROCESSING METHOD AND APPARATUS FOR ANALYSING TIME-DECAY SIGNALS

(75) Inventors: Charles Charbel Harb, Bungendore (AU); Thomas Gary Spence, New Orleans, LA (US); Toby Kristian Boyson, Conder (AU)

(73) Assignee: NEWSOUTH INNOVATIONS PTY LIMITED, New South Wales (AU)

( * ) Notice: Subject to any disclaimer, the term of this patent is extended or adjusted under 35 U.S.C. 154(b) by 1041 days.

(21) Appl. No.: 13/809,569

(22) PCT Filed: Aug. 19, 2011

(86) PCT No.: PCT/AU2011/001071
§ 371 (c)(1),
(2), (4) Date: Feb. 22, 2013

(87) PCT Pub. No.: WO2012/021943
PCT Pub. Date: Feb. 23, 2012

(65) Prior Publication Data
US 2013/0144561 A1  Jun. 6, 2013

(30) Foreign Application Priority Data

Aug. 20, 2010 (AU) .............................. 2010903745

(51) Int. Cl.
*H03F 1/26* (2006.01)
*G01N 21/59* (2006.01)
(Continued)

(52) U.S. Cl.
CPC ................ *G01N 21/59* (2013.01); *G01J 3/42* (2013.01); *G01J 3/4338* (2013.01); *G01J 3/45* (2013.01);
(Continued)

(58) Field of Classification Search
CPC .......... G01N 21/59; G01J 3/42; G01J 3/4338; G01J 3/45
(Continued)

(56) References Cited

U.S. PATENT DOCUMENTS 3,244,978 A * 4/1966 Craven .................. G01R 27/06
324/149
5,973,782 A   10/1999 Bomse
(Continued)

FOREIGN PATENT DOCUMENTS

CN   1290429 A    4/2001
CN   101273535 A  9/2008
(Continued)

OTHER PUBLICATIONS

Hamers, E. et al., "Fourier transform phase shift cavity ring down spectroscopy," Chemical Physics Letters, vol. 365, Iss. 3-4 (Nov. 2002), pp. 237-243.
(Continued)

*Primary Examiner* — Toan M Le
*Assistant Examiner* — Xiuqin Sun
(74) *Attorney, Agent, or Firm* — Kilpatrick Townsend & Stockton LLP

(57) ABSTRACT

Systems and methods for analysing a time-domain signal are described. The method comprising: in a mixer (150), mixing the time-decay signal (115) with a local oscillator signal (122) generated by a local oscillator (120), resulting in a mixed signal from which a Fourier transformed time-decay signal is generated comprising a fundamental transformed time decay signal at the fundamental frequency of the local oscillator signal (122) and a plurality of transformed time-decay signals at a plurality of frequencies; and determining
(Continued)

the magnitude of each of the transformed time-decay signals at the fundamental frequency and at a frequency other than the fundamental frequency.

26 Claims, 13 Drawing Sheets

(51) Int. Cl.
G01J 3/42 (2006.01)
G01J 3/45 (2006.01)
G01N 21/31 (2006.01)
G06F 17/00 (2019.01)
G01J 3/433 (2006.01)
G01N 21/39 (2006.01)
G01N 21/35 (2014.01)

(52) U.S. Cl.
CPC ............ *G01N 21/31* (2013.01); *G06F 17/00* (2013.01); *G01N 21/39* (2013.01); *G01N 2021/3595* (2013.01)

(58) Field of Classification Search
USPC ........................................................ 702/189
See application file for complete search history.

(56) References Cited

U.S. PATENT DOCUMENTS

| | | | | |
|---|---|---|---|---|
| 5,983,121 A | * | 11/1999 | Tsuchiya | ............... G01N 21/49 356/432 |
| 6,356,350 B1 | | 3/2002 | Silver et al. | |
| 7,025,253 B2 | * | 4/2006 | Sinkus | ................... A61B 5/055 324/307 |
| 2003/0189711 A1 | | 10/2003 | Orr et al. | |
| 2006/0027021 A1 | * | 2/2006 | Choi | ...................... G01H 17/00 73/579 |
| 2007/0229834 A1 | | 10/2007 | Patel et al. | |
| 2010/0243903 A1 | * | 9/2010 | Fahr | ................... G01N 21/3563 250/339.08 |
| 2011/0235022 A1 | * | 9/2011 | Majewski | ................ G01J 3/42 356/51 |

FOREIGN PATENT DOCUMENTS

| | | |
|---|---|---|
| EP | 0689045 A1 | 12/1995 |
| JP | H0843204 A | 2/1996 |
| WO | 2005/108939 A1 | 11/2005 |
| WO | 2007/034681 A1 | 3/2007 |

OTHER PUBLICATIONS

Paldus, B. et al., "An historical overview of cavity-enhanced methods," Canadian Journal of Physics, vol. 83, No. 10 (Oct. 2005), pp. 975-999.
Extended European Search Report dated Jun. 1, 2015 in EP Patent Application No. 11817586.8, 10 pages.
Chinese Office Action dated Jul. 8, 2015 in CN Patent Application No. 201180040415.6, 8 pages.
Japanese Office Action dated Jul. 28, 2015 in JP Patent Application No. 2013-524308, 7 pages.
International Search Report dated Nov. 4, 2011, PCT Application No. PCT/AU2011/001071, 2 pages.
First Office Action dated Oct. 29, 2014 in CN Patent Application No. 201180040415.6, 8 pages.

* cited by examiner

OPTICAL SIGNAL PROCESSING METHOD AND APPARATUS FOR ANALYSING TIME-DECAY SIGNALS

CROSS-REFERENCE TO RELATED APPLICATIONS

This application is a National Stage of International Application No. PCT/AU2011/001071, filed Aug. 19, 2011, and which claims the benefit of Australian Patent Application No. 2010903745, filed Aug. 20, 2010, the disclosures of both applications being incorporated herein by reference.

TECHNICAL FIELD

The present invention relates to a detection scheme for analysis of a signal and in particular to a digital detection scheme for analysing optical absorbance signals.

The invention has been developed primarily for use as a digital detection scheme for analysing optical absorbance signals in real time and will be described hereinafter with reference to this application. However, it will be appreciated that the invention is not limited to this particular field of use.

BACKGROUND

Any discussion of the background art throughout the specification should in no way be considered as an admission that such background art is prior art, nor that such background art is widely known or forms part of the common general knowledge in the field.

Absorption spectroscopy is widely used to qualitatively and quantitatively identify chemical species. If a species of interest possesses a unique absorption feature, real-time monitoring of the absorber can be achieved by simply measuring absorbance at a single frequency, or over a single absorption band. However, more often than not, contaminants are present which also absorb light of the same frequency. As a result, real-time spectral analysis of contaminated samples requires collection of absorbance data over a range of wavelengths.

Unfortunately, this approach is commonly hindered by the ability to rapidly extract information from complex absorption data.

Therefore, there is a need for a demodulation technique to extract absorption information from time-varying absorption signals in real time, or at least significantly faster than current spectral analysis systems.

SUMMARY

The following definitions are provided as general definitions and should in no way limit the scope of the present invention to those terms alone, but are put forth for a better understanding of the following description.

Unless defined otherwise, all technical and scientific terms used herein have the same meaning as commonly understood by those of ordinary skill in the art to which the invention belongs. For the purposes of the present invention, the following terms are defined below:

The articles "a" and "an" are used herein to refer to one or to more than one (i.e. to at least one) of the grammatical object of the article. By way of example, "an element" refers to one element or more than one element.

The term "about" is used herein to refer to quantities that vary by as much as 30%, preferably by as much as 20%, and more preferably by as much as 10% to a reference quantity.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The term "real time", for example "displaying real time data", refers to the display of the data without intentional delay, given the processing limitations of the system and the time required to accurately measure the data. Similarly, the phrase "analysing a signal in real time" refers to the analysis of a signal and presentation or output of data representative of the signal without intentional delay, given the processing limitations of the system and the time required to accurately analyse the signal and present the output of such analysis.

According to a first aspect, there is provided a method for analysing a time-decay signal. The method may comprise, in a mixer, mixing the time-decay signal with a local oscillator signal (or modulation signal) output from a local oscillator generator (or modulator). The mixing of the time-decay signal with the local oscillator signal results in a mixed signal from which a Fourier transformed time-decay signal is generated. The Fourier transformed time-decay signal may comprise a fundamental transformed time decay signal at the fundamental frequency of the local oscillator signal. The Fourier transformed time-decay signal may also comprise a plurality of transformed time-decay signals having a plurality of frequency components. At least some of the frequency components may be common to both the local oscillator signal and the time-decay signal of interest. In other arrangements, all of the frequency components of the mixed signal may be common to both the local oscillator and the time-decay signal. The method may further comprise determining the magnitude of each of the transformed time-decay signals at the fundamental frequency and at a frequency other than the fundamental frequency.

In an arrangement of the first aspect there is provided a method for analysing a time-decay signal comprising:

in a mixer, mixing the time-decay signal with a local oscillator signal generated by a local oscillator generator, resulting in a mixed signal from which a Fourier transformed time-decay signal is generated comprising a fundamental transformed time decay signal at the fundamental frequency of the local oscillator signal and a plurality of transformed time-decay signals at a plurality of frequencies; and determining the magnitude of each of the transformed time-decay signals at the fundamental frequency and at a frequency other than the fundamental frequency.

One or more ratios comprising the magnitude of at least one of the transformed time-decay signals with at least one other transformed time-decay signals may be determined. The one or more ratios may be representative of the spectral content of the time-decay signal. The spectral content of the time decay signal may be determined from a calibration curve relating one or more ratios of the at least one of the transformed time-decay signals with at least one other transformed time-decay signal to a parameter comprising information about the spectral content of the time-decay signal. The method may further comprise extracting the spectral content of the time-decay signal from the parameter. The parameter may be the decay time-constant of the time-decay signal.

The method may be repeated a plurality of times for different time-decay signals to obtain the spectral content of each of the different time-decay signals and therefrom determine a spectrum of a sample. The method may further comprise determining from the spectrum one or more characteristics or parameters of the sample. The method may further or alternatively comprise indentifying one or more components of the sample from the spectrum.

The frequencies of the plurality of transformed time-decay signals may be at one or more harmonic frequencies of the fundamental frequency. The method may further comprise determining a ratio of the magnitude of at least one of the transformed time-decay signals at a frequency with the magnitude of either one or more of the remaining transformed time-decay signals or the fundamental transformed time-decay signal.

The time-decay signal may be an absorbance signal. The time-decay signal may be a cavity-ring down signal. The system may be adapted for analysing the time-decay signal (i.e. the absorbance signal or cavity-ring-down signal) in real time. The local oscillator may be a signal generator oscillator and the local oscillator signal may be a square wave. The local oscillator signal may be a sine wave having a desired frequency. The local oscillator signal may be a complex signal waveform comprising a plurality of frequency components. In further arrangements, the time-decay signal may be any form of time-domain signal. The time-domain signal may be an interferogram. The interferogram may be derived from an interferometer.

According to a second aspect, there is provided a system for analysing a time-decay signal. The system may comprise a mixer for mixing the time-decay signal with a local oscillator signal. The mixing of the time decay and local oscillator signals may form a mixed signal from which a Fourier transformed time-decay signal is generated. The Fourier transformed time-delay signal may comprise a fundamental transformed time decay signal at the fundamental frequency of the local oscillator signal. The Fourier transformed time-delay signal may also comprise a plurality of transformed time-decay signals at a plurality of frequencies of the fundamental frequency. The system may further comprise a determiner for determining the magnitude of each of the transformed time-decay signals at the fundamental frequency and at the frequency of each of the plurality of frequencies. The determiner may comprise a computer, a calculator or other suitable hardware or software components adapted for determining and or calculation purposes. The Fourier transformed time-delay signal may be generated by the determiner.

In an arrangement of the second aspect, there is provided a system for analysing a time-decay signal comprising:

a mixer for mixing the time-decay signal with a local oscillator signal to form a mixed signal from which a Fourier transformed time-decay signal is generated comprising a fundamental transformed time decay signal at the fundamental frequency of the local oscillator signal and a plurality of harmonic transformed time-decay signals at a plurality of harmonic frequencies of the fundamental frequency; and a determiner for determining the magnitude of each of the transformed time-decay signals at the fundamental frequency and at the frequency of each of the plurality of harmonic frequencies.

The time-decay signal may be an absorbance signal. The time-decay signal may be a cavity-ring down signal. The system may be adapted for analysing the time-decay signal (i.e. the absorbance signal or cavity-ring-down signal) in real time.

According to a third aspect, there is provided a system for analysing a time-decay signal from an absorbing species in an optical detection system. The system may comprise a mixer for mixing the time-decay signal with a local oscillator signal generated by a local oscillator resulting in a mixed signal from which a Fourier transformed time-decay signal may be generated. The Fourier transformed time-decay signal may comprise a fundamental transformed time decay signal at the fundamental frequency of the local oscillator signal. Fourier transformed time-decay signal may further comprise at least one or a plurality of transformed time-decay signals at a plurality of frequencies of the fundamental frequency. The system may further comprise a determiner for determining the magnitude of each of the transformed time-decay signals at the fundamental frequency and at the frequency of each of the plurality of frequencies. The determiner may comprise a computer, a calculator or other suitable hardware or software components adapted for determining and/or calculation purposes.

In an arrangement of the third aspect, there is provided a system for analysing a time-domain signal from an absorbing species in an optical detection system, the system comprising:

a mixer for mixing the time-domain signal with a local oscillator signal generated by a local oscillator resulting in a mixed signal from which a Fourier transformed time-decay signal is generated comprising a fundamental transformed time-domain signal at the fundamental frequency of the local oscillator signal and a plurality of harmonic transformed time-decay signals at a plurality of harmonic frequencies of the fundamental frequency; and a determiner for determining the magnitude of each of the transformed time-domain signals at the fundamental frequency and at the frequency of each of the plurality of harmonic frequencies.

The time-domain signal may be an absorbance signal. The optical detection system may be a cavity-ring-down optical detection system and the time-domain signal may be a time-decay signal from the cavity-ring down system. In further arrangements, the time-decay signal may be any form of time-domain signal. The time-domain signal may be an interferogram. The interferogram may be derived from an interferometer. The system may be adapted for analysing the time-domain signal (i.e. the absorbance or signal or time-decay signal) in real time.

The excitation source for the optical cavity-ring-down detection system may be chosen from one or more of a continuous wave source, a quasi-continuous wave source or a pulsed source and the excitation source may be a continuous wave laser source, a quasi-continuous wave laser source, a pulsed laser source, or a modulated laser source. For example, the light source may be a quantum cascade laser. The modulated laser source may have a modulation depth of 100% or less than 100%, i.e. the modulation depth may be between 0.01 and 100%, 1% and 100%, 5% and 100%, 10% and 100%, 20% and 100%, 30% and 100%, 40% and 100% or 50% and 100%, and may be about 0.01%, 0.05%, 0.1%, 0.5%, 1.5%, 10%, 15%, 20%, 25%, 30%, 35%, 40%, 45%, 50%, 55%, 60%, 65%, 70%, 75%, 80%, 85%, 90%, 95%, 97%, 98%, 99%, 99.5%, or about 100%. The optical detection system may be an interferometer detection system and the time-domain signal may be an interferogram in time. The interferogram in time may be derived from changes in a parameter over a space (eg. distance) domain over a desired time frame. The local oscillator may be a signal generator oscillator and the local oscillator signal may be a square wave. The local oscillator signal may be a sine wave having a desired frequency. The local oscillator signal may be a complex signal waveform comprising a plurality of frequency components.

In any of the aspects of the methods disclosed herein, the method may comprise a method for analysing an absorbance signal. Aspects of the method may comprise generating a modulation signal in a modulator. Aspects of the method may further comprise modulating a light source with the modulation signal. Aspects of the method may further comprise directing the light signal to a sample which absorbs at least a portion of the light signal to generate an absorbance signal. The absorbance signal may comprise a time decay portion. Aspects of the method may further comprise detecting the absorbance signal with a detector to generate a time-dependent detected signal. Aspects of the method may further comprise mixing the detected signal with the modulation signal to generate a mixed signal. Aspects of the method may further comprise transforming the mixed signal to generate a Fourier transformed time-decay signal. The transforming of the mixed signal may comprise low-pass filtering, integrating or summing of the mixed signal to generate the Fourier transformed time-decay signal. The Fourier transformed time-decay signal may comprise a fundamental transformed time decay signal at the fundamental frequency of the local oscillator signal. The Fourier transformed time-decay signal may comprise at least one or a plurality of transformed time-decay signals having a plurality of frequency components. Aspects of the method may further comprise determining the magnitude of each of the transformed time-decay signals at the fundamental frequency and at least one frequency other than the fundamental frequency to generate a plurality of frequency-dependent magnitude signals. Aspects of the method may further comprise analysing the frequency-dependent magnitude signals to determine data representative of the absorbance signal to determine the absorbance of the sample.

In particular arrangements, the methods disclosed herein may be adapted to analyse an absorbance signal comprising; generating a modulation signal in a modulator; modulating a light source with the modulation signal; directing the light signal to a sample which absorbs at least a portion of the light signal to generate an absorbance signal, the absorbance signal comprising a time decay portion; detecting the absorbance signal with a detector to generate a time-dependent detected signal; mixing the detected signal with the modulation signal to generate a mixed signal; transforming the mixed signal to generate a Fourier transformed time-decay signal comprising a fundamental transformed time decay signal at the fundamental frequency of the local oscillator signal and a plurality of transformed time-decay signals having a plurality of frequency components; determining the magnitude of each of the transformed time-decay signals at the fundamental frequency and at least one frequency other than the fundamental frequency to generate a plurality of frequency-dependent magnitude signals; analysing the frequency-dependent magnitude signals to determine data representative of the absorbance signal to determine the absorbance of the sample.

The analysing of the frequency-dependent magnitude signals may comprise determining a ratio of the magnitude of at least one of the transformed time-decay signals at a frequency with the magnitude of either one or more of the remaining transformed time-decay signals or the fundamental transformed time-decay signal. The ratio(s) of magnitudes may be representative of the time decay constant, $\tau$, of the time-decay signal, which may inturn be representative of an absorbance and/or absorption spectrum of the sample.

In any of the aspects of the systems disclosed herein, the system may be adapted for analysing an absorbance signal. The system may comprise a modulator for generating a modulation signal. The system may further comprise a light source adapted to be modulated with the modulation signal. The system may further comprise an optical cavity. The optical cavity may be adapted to resonate modulated light from the light source and to output the absorbance, wherein the cavity is adapted to accept an absorbing sample therein such that, in use the sample absorbs at least a portion of the resonating light signal. The absorbance signal may comprise a time decay portion. The system may further comprise a detector for detecting the absorbance signal and to generate a time-dependent detected signal. The system may further comprise a mixer for mixing the detected signal with the modulation signal to generate a mixed signal. The system may further comprise a signal transformer for transforming the mixed signal and generate a Fourier transformed time-decay signal. The signal transformer may comprise a low-pass filter, integrator or sum operator. The Fourier transformed time-decay signal may comprise a fundamental transformed time decay signal at the fundamental frequency of the modulation signal. The Fourier transformed time-decay signal may comprise at least one or a plurality of transformed time-decay signals having a plurality of frequency components. The system may further comprise a determiner for determining the magnitude of each of the transformed time-decay signals at the fundamental frequency of the modulator and at least one frequency other than the fundamental frequency to generate a plurality of frequency-dependent magnitude signals. The system may further comprise an analyser for analysing the frequency-dependent magnitude signals to determine data representative of the absorbance signal to determine the absorbance of the sample.

The system may comprise a second modulator (local oscillator) of a second (different) modulation frequency. The system may comprise a second mixer for mixing the detected time-dependent detected signal with the second modulation frequency to generate a second mixed signal. The signal transformer may transform the second mixed signal to generate a second Fourier transformed time-decay signal at the second modulation frequency. The determiner may determine the magnitude of the second Fourier transformed time-decay signal at the second modulation frequency. The analyser may determine a ratio of the magnitude of the second Fourier transformed time-decay signal with the magnitude of the first Fourier transformed time-decay signal.

In particular arrangements, the systems disclosed herein may be a system for analysing an absorbance signal comprising: a modulator for generating a modulation signal; a light source adapted to be modulated with the modulation signal; an optical cavity adapted to resonate modulated light from the light source and to output the absorbance signal, wherein the cavity is adapted to accept an absorbing sample therein such that, in use the sample absorbs at least a portion of the resonating light signal, and the absorbance signal which comprises a time decay portion; a detector for detecting the absorbance signal and to generate a time-dependent detected signal; a mixer for mixing the detected signal with the modulation signal to generate a mixed signal; a signal transformer for transforming the mixed signal and generate a Fourier transformed time-decay signal, wherein the Fourier transformed time-decay signal comprises a fundamental transformed time decay signal at the fundamental frequency of the local oscillator signal and at least one or a plurality of transformed time-decay signals having a plurality of frequency components; a determiner for determining the magnitude of each of the transformed time-decay signals at the fundamental frequency and at least one frequency other than the fundamental frequency to generate a plurality of frequency-dependent magnitude signals; and an analyser for analysing the frequency-dependent magnitude signals to determine data representative of the absorbance signal to determine the absorbance of the sample.

The systems disclosed herein may be adapted for real time analysis of the absorbance signal.

Although any methods and materials similar or equivalent to those described herein can be used in the practice or testing of the present invention, preferred methods and materials are described. It will be appreciated that the methods, apparatus and systems described herein may be implemented in a variety of ways and for a variety of purposes. The description here is by way of example only.

BRIEF DESCRIPTION OF THE DRAWINGS

Arrangements of the detection scheme described herein will now be described, by way of an example only, with reference to the accompanying drawings wherein.

DETAILED DESCRIPTION

Figure 1:
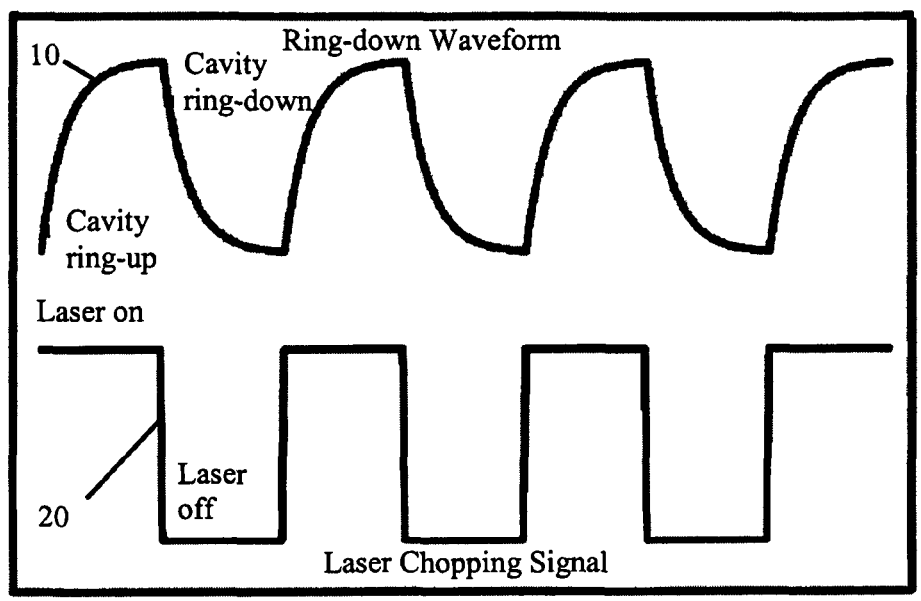
FIG. 1 is a plot of a time-decay signal and a typically square wave modulation signal used in a CRDS system.

With reference to the drawings, disclosed herein are systems and methods for digital detection for analysis of a time-decaying signal, exemplified herein to the detection and analysis of optical absorbance signals.

As will be appreciated, any waveform may be represented by a weighted sum of sines and cosines. In electronic systems, the extent to which a sine wave of a given frequency contributes to an arbitrary waveform may be determined by using a mixer which may be either analog or digital. A mixer accepts as inputs a signal waveform and a signal generated by a local oscillator, which is commonly either a sine function of known frequency f or a square wave signal. The DC component of the mixer output is a signal proportional to the extent to which a sine wave of frequency f contributes to the signal waveform. By scanning the local oscillator frequency, a complex signal in time can be decomposed into a frequency-domain spectrum analogous to that obtained by applying a Fourier-transform.

Using a sine wave as the local oscillator of a mixer, the contribution of only a single frequency component to a signal waveform is measured. If several frequencies are of interest, then an alternate local oscillator may be used to simultaneously measure contributions of a set of sine waves having different frequencies. For example, a square wave of frequency f is composed of a set of sine waves whose frequencies are f, 3f, 5f, 7f, 9f, . . . . With a square wave as the local oscillator signal, the mixed signal obtained from the output of the mixer is therefore a measure of the combined contribution of sine waves at f, 3f, 5f, 7f, 9f, or higher harmonics to the signal waveform. In this way, a mixer can be used to determine the simultaneous contributions of a set of sine functions to a signal waveform. Therefore, by using an appropriate local oscillator signal waveform, the contribution of a set of sine waves to a complex waveform may be quickly determined. It should be noted that this detection scheme has the advantage of filtering out all noise sources except those which happen to occur at f, 3f, 5f, 7f, 9f, and higher harmonics.

Whilst not limited to the analysis of signals typically obtained from a locked cavity ring-down spectroscopic system (eg. similar to plot 10 of FIG. 1) the signal analysis technique described herein is readily described with reference to a time-domain signal, for example for analysis of an interferogram (i.e. from an interferometer), or alternatively for analysis of signal degeneration in an optical communications system (e.g. for transport of optical modulated signals over a communications links such as in free-space or optical fibre).

In a CRDS system, the sample (absorbing material) is placed in a high-finesse stable optical resonator or ring-down cavity having an input coupling mirror and an output coupling mirror. Light admitted into the ring-down cavity through the input coupler circulates back and forth multiple times setting up standing waves having periodic spatial variations. Light exiting through the output coupler is proportional to the intra-cavity light intensity. After the input light source is terminated, the radiant energy stored in the ring-down cavity decreases in time (rings-down). For an empty cavity, the stored energy follows an exponential decay characterized by a ring-down rate that depends only on the reflectivity of the mirrors, the separation between the mirrors and the speed of light in the cavity. If a sample is placed in the resonator, the ring-down is accelerated; under suitable conditions, the intra-cavity energy decays almost perfectly exponentially.

In cavity ringdown spectroscopy (CRDS), the decay of light trapped in the high-finesse optical cavity is a direct measure of absorbance (also known as optical density) by gas-phase molecules within the cavity. Absorbance is measured by monitoring the decay constant, $\tau$, of a signal, I, which is decaying exponentially in time, t, described by:

$$I = O + A \cdot \exp[-t/\tau] \quad \text{(Equation 1)}$$

where O is an arbitrary DC offset, A is the amplitude of ring-down waveform. The ring-down decay constant, $\tau$, is inversely proportional to absorbance within the optical cavity. An absorption spectrum for the sample is obtained by plotting the ring-down rate R or the reciprocal of the ring-down decay constant $1/\tau$ versus the wavelength $\lambda$ of the incident light. In practice, the decay constant $\tau$ is almost universally determined by digitizing the signal at the output of the cavity and fitting individual or average ring-down waveforms to a three parameter function such as that of Eq. 1 using a non-linear least squares fitting routine.

Unfortunately, this process greatly reduces the speed of any instrument attempting to provide real-time spectra over more than a few wavelengths. Two early groups (see for example references 1 and 3) avoided fitting the ring-down signal by using analog systems. Anderson et al. (Reference 1) used a clock circuit to determine r, whereas Romanini et al. (Reference 3) utilized a boxcar integrator. Both methods, although good at rapidly extracting data, are disadvantaged by the fact that the methods only sample a small section of the ring-down signal; thus, the signal to noise ratio is necessarily compromised. Further discussion of analog CRDS detections systems is provided in U.S. Pat. Nos. 6,233,052 and 6,532,071.

Instruments employing continuous-wave (cw) lasers frequency-locked to the ring-down cavity are capable of generating waveforms at rates exceeding 5 kHz (see for example, references 4 and 5). In these systems, the laser and optical cavity are locked in resonance and the time limiting factor in the acquisition of ring-down waveforms is $\tau$ itself, i.e. waveforms like plot 10 of FIG. 1 may be generated as fast as the cavity can "ring up" and "ring down." Only one instrument (see for example the instrument of Reference 4) has demonstrated the ability to extract real-time absorption data (i.e. absorbance and/or absorption spectra) from ring-down waveforms at these rates. This system employed an analog detection system consisting of a logarithmic amplifier, analog filters and a lock-in amplifier, however since the system requires such an array of specialised components the system is necessarily and complex and therefore can be difficult to use such that meaningful results are obtained.

To simplify the detection scheme it is recognised that there are two limiting cases for the time decay signal when turned on and off at a fundamental frequency f (i.e. the laser chopping signal shown in plot 20 of FIG. 1).

Figure 2A:
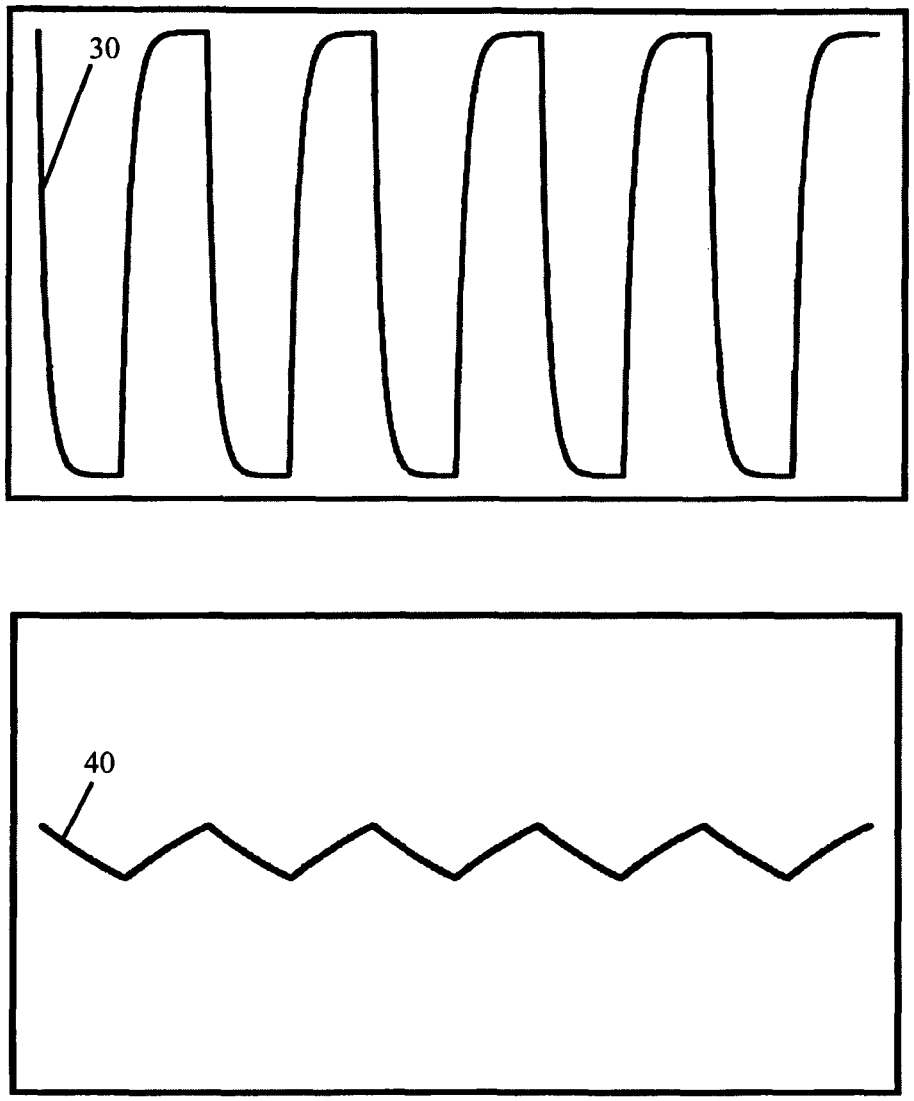
FIG. 2A shows a depiction of time-decay signals at the limiting cases of ring-down waveforms generated by a laser/cavity locked system.

FIG. 2A is a schematic diagram showing signals at the limiting cases of ring-down waveforms generated by a laser/cavity locked system. As one can see in plot 30 of FIG. 2A in the limit of very short decay times $\tau$ compared to the optical chopping frequency f (i.e. small $\tau$, or large sample absorbance) the ring-down waveform of a frequency-locked ring-down system approaches a square wave (this waveform will herein be referred to as a quasi-square wave). At long decay times i.e. plot 40 of FIG. 2A (large $\tau$, low sample absorbance) the ring-down waveform approaches a triangle wave (i.e. a quasi-triangle wave).

Figure 2B:
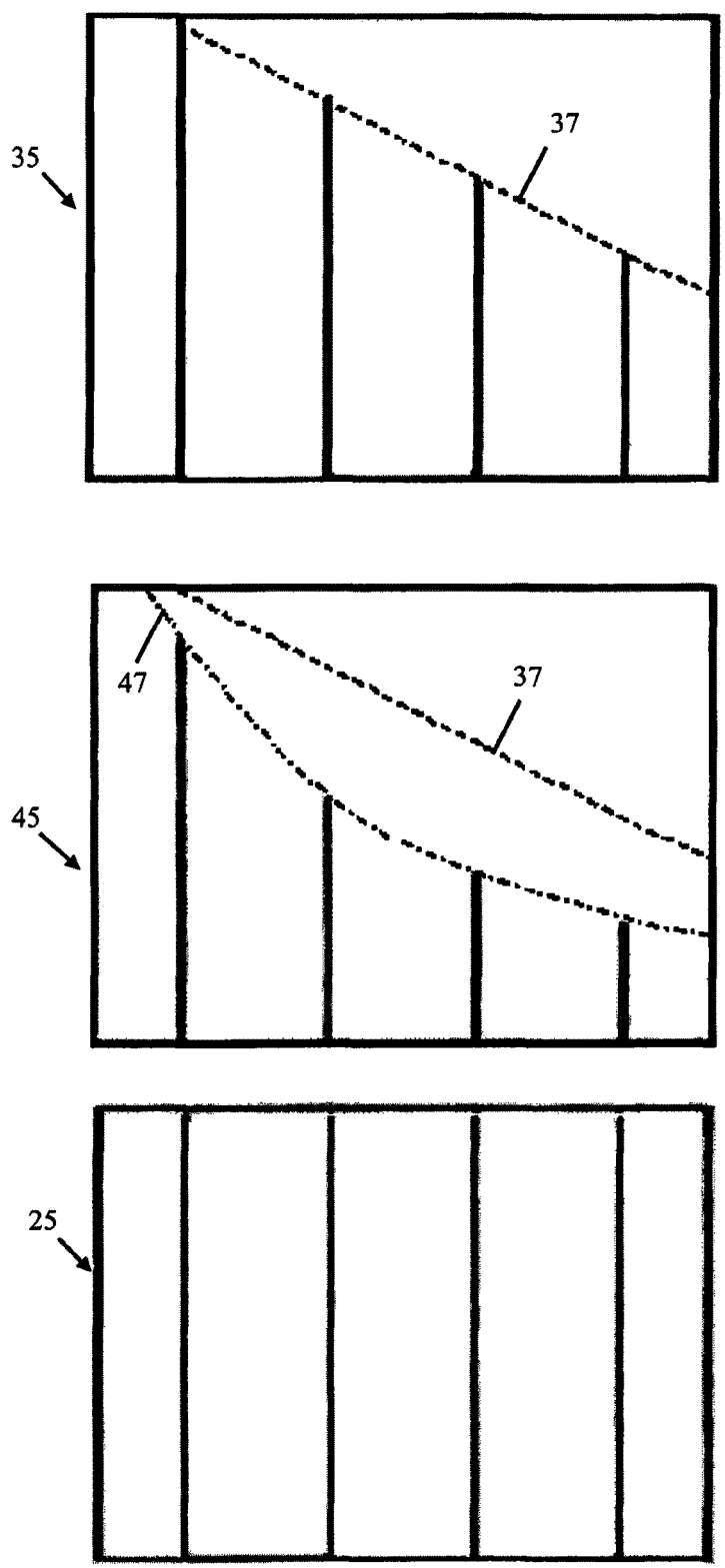
FIG. 2B shows a depiction of the Fourier transform of each of limiting waveforms of FIG. 2A and a square wave.

The Fourier transform of each of these limiting waveforms (i.e. quasi-square wave and quasi-triangle wave) and also that of a pure square wave are respectively shown in plots 35, 45 and 25 in FIG. 2B and there are several things to note about the frequency components of these two limiting cases. First, the frequencies f of the component sine waves which make up the Fourier spectrum of the time-decay waveforms are the same for both waveforms. Second, the amplitudes of all frequency components for the waveform with short decay time are generally lower than those for the long-$\tau$ waveform. That is, the envelope 47 of the magnitudes of the harmonic components in the Fourier transformed signal for the quasi-triangle time decay waveform 40 is of lesser magnitude than the envelope 37 of the magnitudes of the harmonic components in the Fourier transformed signal for the quasi-square time decay waveform 30. This decrease in the magnitude of each of the harmonic components is due in part to the lower amplitude of the short-$\tau$ waveform 40 which is a result of neither allowing the cavity to fully ring-up or ring-down.

Furthermore, the amplitudes of the higher-frequency components of the long-$\tau$ waveform 40 are larger than for the short-$\tau$ case as clearly evidenced in the comparison of the envelopes 37 and 47 in FIG. 2B. This is a result of the shape of the waveforms themselves, a square wave is composed of a set of equally weighted sine waves (see the equal magnitudes of the harmonic components in the Fourier transformed signal 25 of a pure square wave) whereas a triangle wave is composed of a set of sine waves whose intensities decrease at higher frequencies.

Therefore, changes in the decay time $\tau$ of the time-decay signal can be determined by monitoring the magnitude of one or more of the various frequency components of the ring-down waveform, for example, one or more harmonic components of the fundamental modulation frequency f of the CRDS system. This is performed in practice for an appropriate local oscillator local oscillator either using a mixer or digitally by multiplying the ring-down signal and the local oscillator signal and summing over a given time. In the case where the intensity of the laser output in the CRDS system is constant or only slowly varying as the frequency of the laser is scanned, the total amplitude of all frequency components (e.g. harmonic frequencies of the fundamental modulation frequency f) of the waveform is a measure of the decay time $\tau$. To simultaneously measure all frequency components, the ring-down waveform is mixed with the appropriate local oscillator signal, which is advantageously taken as the same square wave signal used to modulate the laser intensity in the CRDS system.

As shown in FIG. 2B, the frequency components of the square wave laser modulation signal (i.e. the chopping frequency of the laser) occur at the same frequencies as the components of the ring-down waveform. Therefore, by using the laser modulation signal as the local oscillator signal in the mixer, the magnitudes of all the harmonic frequencies of interest are simultaneously measured. In practice, harmonic frequency components up to about the $7^{th}$ or the $9^{th}$ harmonic of the fundamental modulation frequency f are adequate for obtaining an accurate determination of the decay constant $\tau$ with respect to the Fourier components of the time-decay signal. Alternatively, instead of simply taking the magnitude of one or more of the harmonic components and performing a ratio of each of these one or more components with the magnitude of the fundamental Fourier component, a sum of one, two, three, four, five, six, seven, eight, nine, ten or more of the higher-order harmonic components may be taken, and a ratio of the harmonic magnitudes sum taken with the magnitude of the fundamental Fourier component.

Figure 3:
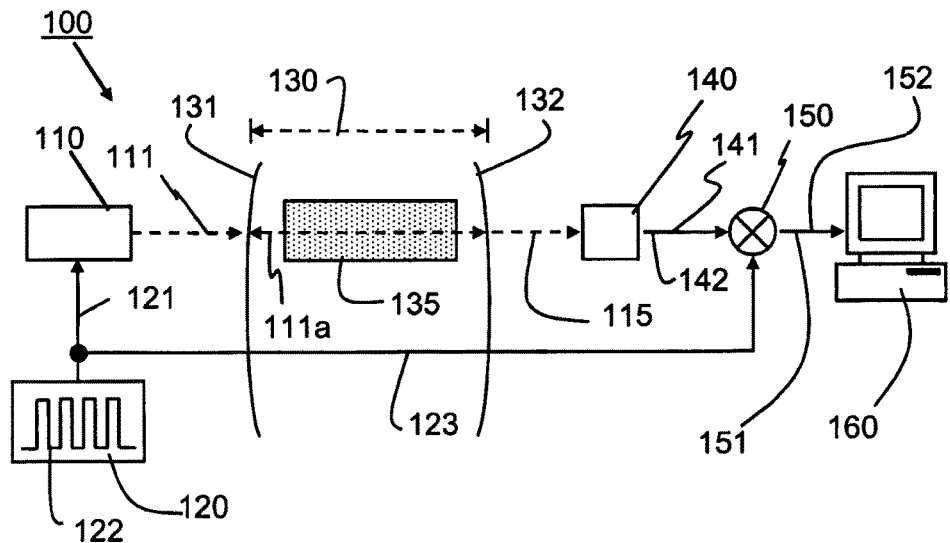
FIG. 3 is a simplified schematic of an exemplary arrangement of a digital demodulation system 100 employed in a CRDS application.

FIG. 3 depicts a simplified schematic of an example arrangement of a system 100 for analysing a time-decay signal depicted in a CRDS application. Light source 110 (for example a suitable laser source), which may be a tunable laser source, is modulated by a square wave signal 122 from a modulator (local oscillator) 120 over communication line 121 to produce a quasi-continuous wave optical beam 111. For example, the light source 110 may be a quantum cascade laser. Other types of light sources and in particular lasers are described hereinafter. The beam 111 enters a high finesse optical cavity 130 defined by reflectors 131 and 132, where each of the reflectors has a reflectivity at the wavelength of the modulated optical beam 111 which is typical for CRDS systems, typically greater than 99.9%, such that the optical beam 111a resonates within the cavity 130. An absorbing sample 135 under analysis (for example, a gas-phase species) is located intermediate the reflectors 131 and 132 within optical cavity 130 such that the optical beam 111 is at least partially absorbed in the cavity 130 by the sample 135. With each round trip of the cavity 130, a small portion of the optical beam 111a exits the cavity as a time-decay signal 115 (having a form similar to that of plot 10 of FIG. 1), and is detected by an optical detector 140. Detector 140 may be, for example, a photomultiplier tube, photodiode or other suitable optical detector having a response time fast enough for detection of the time-decay signal. The detected signal 141 is output from the detector 140 and input via a communication line 142 to a mixer module 150 where the detected signal 141 is digitally mixed with a square wave having the same frequency as the ring-down waveform 115 which may be taken, as depicted here, directly from the square wave modulation signal 122 output from the modulator 120 via a communication line 123. The mixer 150 may generate a transformed (demodulated) output signal 151 which is input via a communication line 152 to a determiner 160 (such as, for example, a computer or alternative determining device such as a calculator or similar device) adapted for analysing the transformed output signal 151. Presently described system 100 is an example of a digital demodulation system for analysing the cavity-ring-down time-decay (absorbance) signal 115 of the sample 135 situated in the optical cavity 130.

In practice, the light source 110 is typically a tunable laser source that is scanned over a frequency range of interest, and the absorbance is determined for frequencies within the scanned frequency range to generate an absorbance spectrum of the absorbing species (sample 135) over the scanned frequency range. Alternatively the light source may be a broadband light source, which outputs light in a range of frequencies, and the system may further comprise a scanning device (not shown) to scan across the range of output frequencies to thereby detect time-decay signals across the scanned frequencies to generate an absorbance spectrum of the absorbing species (sample 135) over the scanned frequency range.

Figure 4:
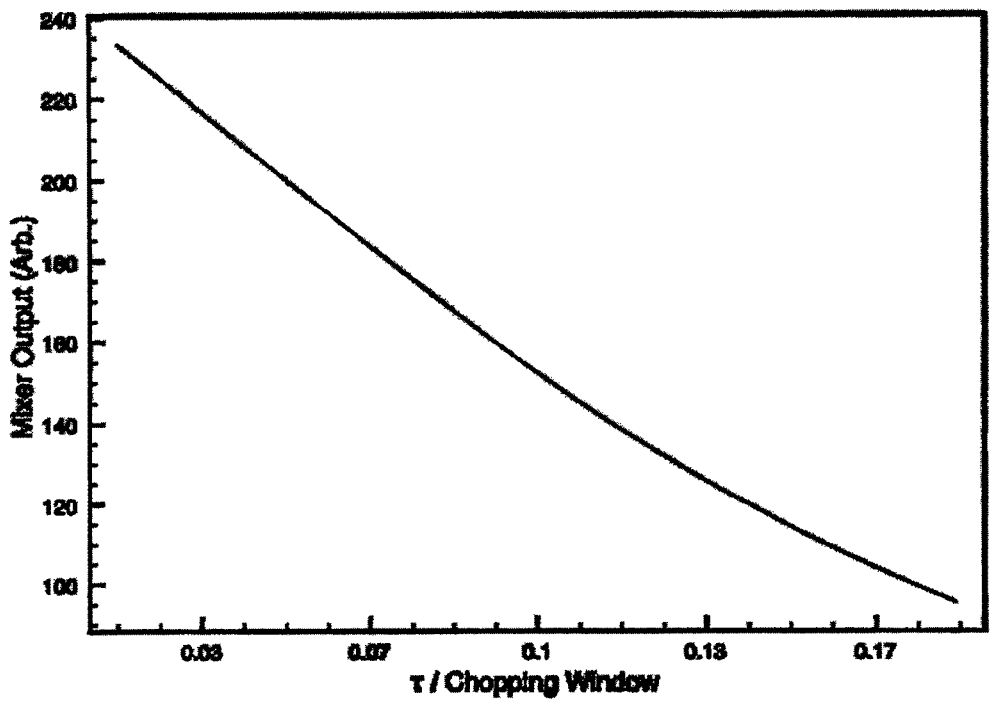
FIG. 4 is a plot of the output of the digital mixer of the arrangement of FIG. 3 against the decay constant.

FIG. 4 is a plot of the output 151 of the digital mixer 150 (whose signal input is the ring-down waveform 115 with varying $\tau$) against the decay constant $\tau$, which is given here as a ratio of $\tau$ to the length of time the cavity is allowed to ring down (the chopping window). This is used as a calibration curve for making the quantitative connection between the ratio between the magnitude of the frequency components in the mixed signal and absorbance in the cavity. It is clear that, while not a linear relationship, the output of the mixer does vary with changes in the decay time $\tau$ of the cavity (determined by the amount of absorbance of the light by a gas-phase species within the cavity 130). The output 151 from the mixer 150 can therefore be used for the determination of the absorbance of the species within the cavity 130. This is most likely performed through the use of a look-up table or calibration curve such as that in FIG. 4 (see for example an experimentally-determined analogous calibration curve in FIG. 10) equating the output from the digital mixer (or the output normalised to the chopping window as shown in FIG. 3) to a decay constant $\tau$, which is expected and appears to follow an exponential relationship, the parameters of which are likely to be a simple function of sampling frequency and sample length. The calibration curve is then used to determine the absorbance of the gas species within the high finesse cavity in the normal manner as for cavity ring-down spectrometer systems, which would be appreciated by the skilled addressee.

One drawback to the system described above is that the output from the digital mixer 150 is sensitive to fluctuations in the laser intensity. As a result, laser fluctuations will act as a noise source in the determination of the decay constant $\tau$. To counter this and make the output from the mixer 150 insensitive to fluctuations in the laser intensity, a ratio of the intensity (magnitude) of one of the higher-frequency components to that of the intensity (magnitude) of a lower-frequency component, i.e. the ratio of the second peak to the first peak in the Fourier transforms of the ring-down waveforms shown in FIG. 2A, is determined. Alternatively, a ratio of the magnitude of one or more of the higher harmonic components (e.g. 3f, 5f, 7f, 9f, . . . ) in the Fourier transformed output to that of the magnitude of the component at the fundamental frequency f is determined.

Figure 5:
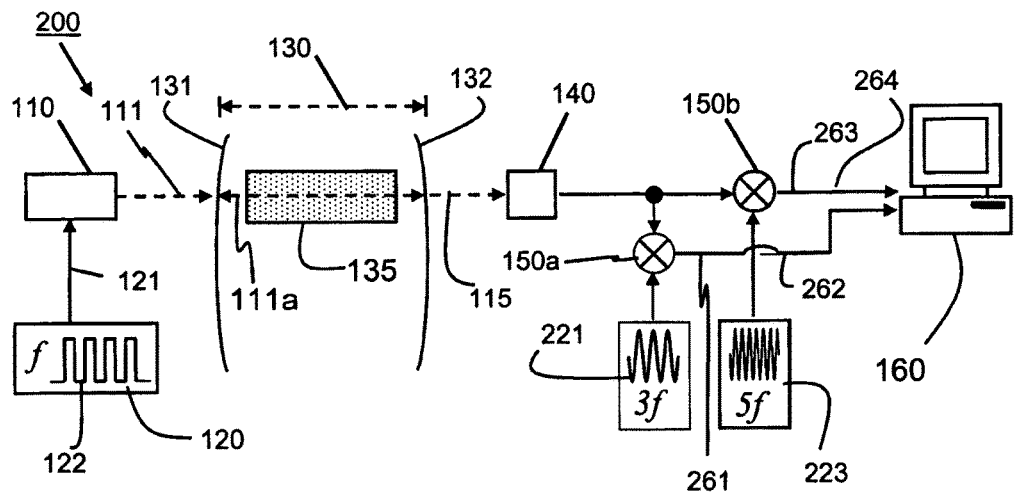
FIG. 5 is an alternate arrangement of a digital demodulation system 100 employed in a CRDS application.

The magnitude of the harmonic components may alternately be obtained using a set of digital mixers as depicted in the alternate schematic arrangement 200 of FIG. 5, where like numerals are used to denote like components of the CRDS system. The system comprises local oscillators 221 and 223 which generate local oscillator signals at one or more frequencies of interest. The frequencies of interest in the local oscillator signals that are generated by the local oscillators 221 and 223 may be harmonic frequencies of the fundamental frequency, although this is not required. Any desired local oscillator generating a signal having one or more frequency components can be chosen for each of the local oscillators e.g. a square wave local oscillator signal or a signal comprising the superposition of one or more sine waves of different frequencies may also be used. The frequencies of the signals generated by the local oscillators need to be frequency components of the waveform of interest, and whilst these frequencies tend to be harmonics, the frequencies of the local oscillator signal are not limited to such harmonics. The local oscillators 221 and 223 are coupled respectively to separate digital mixers 150a and 150b respectively to obtain output signals 261 and 263 indicative of the magnitude of the harmonic component at each frequency which are input to the determiner 160 via communication lines 262 and 264 respectively. By taking the ratio of peaks in the mixed and integrated output (i.e. the Fourier transformed signals), fluctuations in the decay time constant τ caused by intensity fluctuations of the light source 110 are eliminated.

Figure 6:
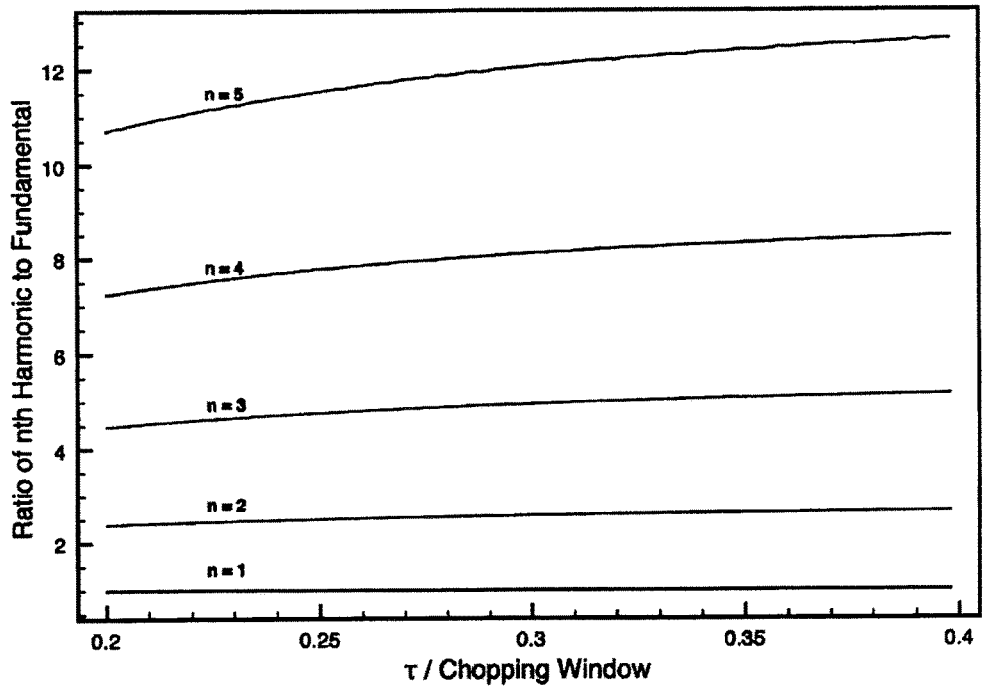
FIG. 6 is a is a plot showing how the ratios of the magnitudes of various higher-order harmonic peaks nf in the Fourier-transform spectra to the magnitude of the fundamental frequency f vary as a relative function of the decay constant $\tau$.

FIG. 6 is a plot showing how the ratios of the magnitudes of various higher-order harmonic peaks of in the Fourier-transform spectra to the magnitude of the fundamental frequency f vary as a relative function of the decay constant τ with respect to the chopping window as above.

Whilst the discussion above has focused on CW-laser output waveforms, the digital signal demodulation technique is also applicable to pulsed-laser systems. Following acquisition by a fast digitizer, a waveform like that of plot 10 in FIG. 1 can be constructed and analysed in the same way using pulsed system ring-down waveforms. In this analysis, most of the data in between ring-down events is eliminated and every other waveform is modified to produce a periodic waveform which is analysed with the appropriate local oscillator signal. The resulting system is capable of acquiring and analysing 100% of waveforms generated by even a fast pulsed system.

This type of digital analysis provides several significant advantages over previous systems. First, all noise sources not coinciding with the set of frequencies in the local oscillator signal generated by the local oscillator are completely filtered out. Indeed, the decay constant τ may be determined quite precisely even in the presence of significant stochastic noise in the time-decay waveform itself. Second, signal offset does not affect the measured τ. Unlike in the analog system mentioned above, so long as the local oscillator (a digitally generated signal) is AC coupled, changes in the DC offset of the ring-down waveform do not affect the observed decay constant using this digital mixing method. Third is speed. By employing digital hardware; such as a field programmable gate arrays, even parallel processes needed to obtain the ratios of intensities as described above can happen at the same rate as the digitizers used to acquire the signal and can be performed at the modulation rate f of the light source itself. This enables in many cases a measurement to be taken in 10 cycles or less (i.e. using between one and ten, or only one, two, three, four, five, six, seven, eight, nine or ten signal waveforms from the CRDS system) and it is envisaged that each measurement can be obtained in 10 milliseconds or less thereby enabling thousands of individual measurements to be taken in under a second compared with the previously reported analog-type systems which could take at most a single measurement each second (if the cycles are particularly noisy, then additional cycles may be required, for example up to 50 or 100 cycles). Thus, for a tunable laser source that is scanned over a frequency range of interest, an entire spectrum of an absorbing species can be taken in under one second thereby significantly speeding up the detection process and enabling complete spectral analysis at significantly faster rates than existing systems. Fourthly, this digital demodulation technique offers noise advantages over the previously reported analog-detection systems. In an analog detection system, every step of analysis adds electronic noise to the waveform. Here, the signal is immediately digitized and all analysis is performed in a completely digital fashion which adds no additional noise to the signal. Furthermore, the system is insensitive to all noise sources which occur at frequencies other than those of the local oscillator signal generated by the local oscillator.

Figure 7:
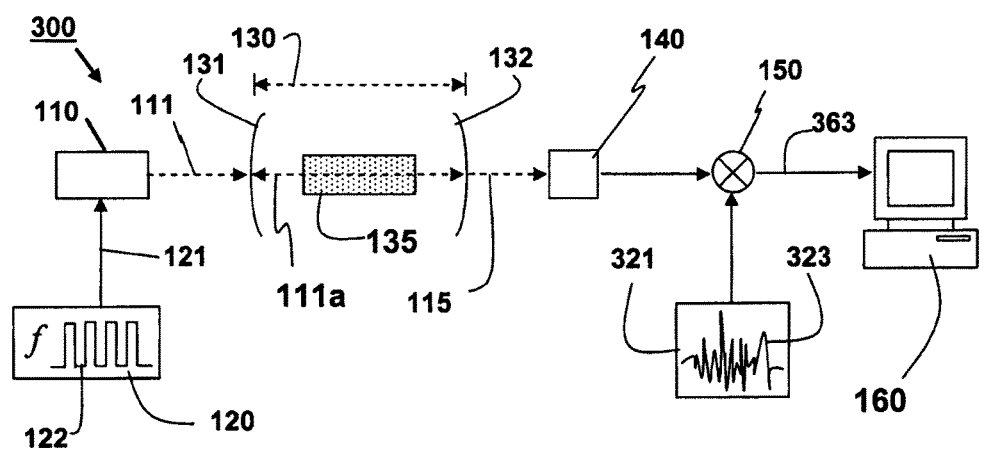
FIG. 7 is a further alternate arrangement of a digital demodulation system 100 employed in a CRDS application.

In a further arrangement 300 as schematically depicted in FIG. 7, which is envisaged as an extension of the arrangement 200 depicted in FIG. 5, the local oscillator 321 may be adapted to generate an arbitrary complex local oscillator signal waveform 323 (which can be formed, for example, from a superposition of sine waves of various frequencies and magnitudes) which is then mixed with the time-decay signal output 115 from the cavity 130 which is detected by detector 140. The output 363 from the digital mixer 150 in this case gives an indication of the magnitude of the combination of frequency components of the arbitrary waveform that is present in the time-decay signal 115 from the cavity 130. In this arrangement, rather than the local oscillator signal simply being used to measure the contribution of a particular frequency to the time-decay signal, the local oscillator signal with a complex local oscillator signal waveform such as waveform 323 will provide a measurement of all the frequency components of the complex local oscillator signal waveform simultaneously and enable determination of the contribution of the set of frequencies to the time-decay signal, or alternatively to a spectrum with an unknown contribution of the local oscillator complex signal waveform thereto. A simple example of this would be to generate an inverse Fourier transform of the known absorbance of a particular species, and use this inverse Fourier-transformed signal as the local oscillator for the system to determine the contribution to the time-decay signal from that species and therefore determine the concentration of the particular species present in the measurement system.

In a further arrangement still, a spectrum of an absorbing species may be obtained using the methods described above using a square-wave modulated signal as the local oscillator, which is advantageously the same modulation signal used for modulation of the laser source so that noise sources in the laser are removed from the resulting Fourier-transformed signal (the output from the mixer module). To obtain the spectrum a tunable laser source is employed and at least one ring-down signal is measured by the detector at each wavelength in the region of interest. In practice more than one ring-down signal may be obtained and the results averaged, although it is envisaged that accurate measurements are possible with between 1 and 10, 1 and 20, 1 and 50 ring-down waveform signals per wavelength—the actual number of waveforms required will of course be dependent upon the noise level in the signals.

Once the absorbance spectrum has been obtained in the wavelength region of interest (refer to the example below) then this spectrum containing an unknown contribution of a (potentially) unknown gas-phase species can be analysed further using the same method repeated. That is, the measured absorbance spectrum is mixed with a local oscillator signal comprising a complex signal waveform which is indicative of the known absorbance spectrum of a species that is suspected of being present in the measured spectrum. This is an application of the generalised Fourier transform technique as would be appreciated by the addressee skilled in digital demodulation techniques. The result of the generalised Fourier transform technique is a measure of the orthogonality of the measured absorbance spectrum with the known absorption spectrum of the suspected species as a function of the percentage probability of the presence of the suspected species in the measured spectrum. If the constituent species of the gas-phase substance being measured by the present systems are unknown, then a plurality of known absorbance spectra from a suitable database (such as HITRAN for example (reference 12), although care would be required in simulating the absorbance spectrum obtained from the database to match with the measurement conditions in the spectrometer (e.g. temperature for example).

Advantageously, a preferred method of obtaining the known absorbance spectra would be to use data acquired from the spectrometer itself. This is particularly suitable for detection of larger and more complex molecules than those that current database systems such as the HITRAN database are able to predict. That is, to build up a library of spectra using the same equipment before any attempt to analyse unknowns. The known absorbance spectra may then each be separately mixed with the measured spectrum in the manner described herein and, depending on the orthogonality of each of the known spectra with that of the measured spectrum, the composition of the measured species may be determined, i.e. this technique find particular advantage in fingerprint analysis with much faster processing speeds. Therefore, the digital signal demodulation technique described above provides a simplified digital method for interrogating high-speed ring-down cavity waveforms using digital demodulation techniques to extract absorbance measurements in real time.

This technique is of course not limited simply to the determination of absorbance in a gas phase species via CRDS, but is applicable to any time-domain signals where a change in intensity at one or more frequencies is a signal indicative of a parameter of the overall system from which the time-domain signal is generated, For example, the above described technique may also be applied in the application of molecular fingerprinting as described below with reference to a Fourier transform infrared (FTIR) interferometer where the measurement is no longer a measurement of a decay in time, but rather highlighting that the local oscillator signal need not be a single sine wave. A very complex local oscillator signal can be constructed with many frequency components to simultaneously, and very rapidly, measure the amplitude of a great number of frequencies of interest in any time-varying signal.

In a particular example, the above digital demodulation technique is applied to a Fourier-Transform Infra-red Spectroscopy application as described below.

In FTIR spectroscopy, light from an incoherent source is passed through a Michelson interferometer and a sample before falling onto a detector. The signal at the detector is monitored as a function of mirror position within the interferometer and a Fourier transform is applied to the resulting interference pattern (interferogram). The result is an intensity spectrum of the light source in frequency space. Placing an absorbing sample in the light beam attenuates the light source and the resulting spectrum exhibits this attenuation. From spectra obtained with and without the sample in the beam, a sample's absorption spectrum is obtained. FTIR spectra of a single gas-phase species commonly exhibit tens if not hundreds of peaks in the absorption spectrum, each containing information about the concentration of the absorbing species. Using the demodulation technique described here, the attenuation of the light source at all frequencies of interest may be rapidly determined.

Ideally, to extract quantitative information from an FTIR spectrum one would use every point in the spectrum at which absorption by the sample is observed. In a simple situation where a set of absorption peaks can be attributed to the absorbing species of interest, the total integrated area under the peaks is commonly used. Several multivariate techniques have been developed to quantitatively determine the concentration of species in mixtures (refer to references 6 to 8). These techniques include classical least squares regression (CLS), inverse least squares regression (ILS), and principle component analysis (PCA). All of these techniques use a set of absorption spectra of the species of interest of known concentration. These spectra are most commonly acquired with the same instrument used to perform the analysis of the unknown, although computed spectra have also been used. This set of spectra is then used to "train" a matrix which in turn is used to extract concentration information from the spectrum of an unknown mixture. All of these methods suffer the same major limitation which restricts the sensitivity all such absorption measurements. Namely, at low concentrations absorption spectroscopy is reduced to measuring a very small change in the observed intensity of the light source. Additionally, deformation of peak shape, including the formation of satellite peaks caused by the Fourier transform of a finite data set i.e. choice of window for the Fourier transform which adds undesirable artefacts to the Fourier transformed signal (see Reference 13 for further discussion of undesired artefacts that may be introduced by Fourier-transforms of discrete datasets). Indeed a great variety of apodisation methods have been developed to minimize satellite peaks and peak deformation in attempts to counter these problems.

In principle, analysis of the interferogram generated by an FTIR instrument offers a way to overcome the limitation imposed by measuring differences in radiant intensity with and without a sample present. In the absence of a sample, the emission spectrum of the light source in an FTIR is generally a broad smooth curve and the resulting interferogram only shows significant intensity at small mirror displacements. As absorbers are placed in the beam, sharp absorption features appear in the absorption spectrum characterized in the time-domain interferogram by high-frequency waveforms which persist for much larger mirror displacements. As a result, frequency-specific detection of signals generated by sharp absorption features becomes a near zero-background measurement at large mirror displacements.

Various groups have previously used methods for analysing interferograms generated in FTIR spectroscopy (see references 9, 10 and 11) and the typical solution is to do time-space Fourier transform analysis by band-pass filtering and often employing multivariate techniques like those described above to analyse interferograms rather than absorption spectra. For example, Brown and co-workers (reference 10) employed a Kalman filter to obtain concentration data using matrices based on a training set of absorption spectra of the absorbing species of interest. Small et al. (reference 9) developed a two-step method for the direct analysis of interferograms applied to environmental monitoring of heated plumes using passive FTIR spectroscopy. First, a digital bandpass filter is applied to the interferogram effectively removing signals outside of the frequency range of interest. Sections of the resulting filtered waveform are then subjected to a numerical pattern recognition algorithm to detect the presence of species such as ammonia and ethanol. Also, Stallard et al. (reference 11) have used a filtered interferogram from an FTIR to generate a synthetic background for use in applications where background spectra can not easily be obtained. They filtered the interferogram by multiplying the waveform by a Gaussian centred at the centerburst, effectively eliminating narrow peak signals from the absorbing species which occur at larger mirror displacements. Each of these earlier methods suffer from problems in the data analysis, most prominently in the time required to obtain their results, problems with artefacts in the data from the bandpass, lowpass, or other filtering methods and the complexity of the system. That is; it would require a skilled operator to perform the calculations in the techniques prior techniques described above, which are representative of the present analysis methods currently in use. Alternatively, if the computations required of the system were automated, this would require an expensive system with a large amount of computational power requirements. As the present method is essentially only performing a multiplication it is considerably less computationally expensive and provides significant advantage in the time required and the ease of use for the operator to enable real-time operation, for example real-time spectral analysis of an absorbance signal at many wavelengths/frequencies.

EXAMPLE 1

Figure 8A:
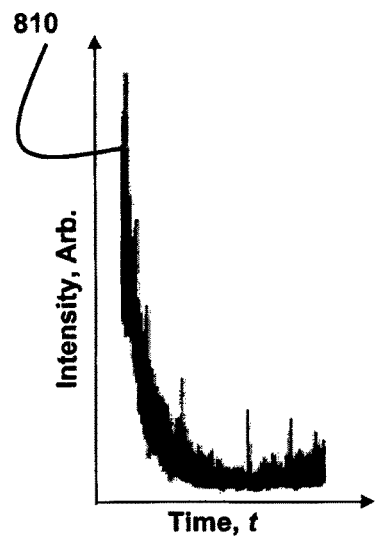
FIGS. 8A and 8B are cavity ring-down signals measured from the output of a high finesse optical cavity in a CRDS system respectively for a) an evacuated cavity and b) a cavity with an unknown concentration of a gas-phase absorbing species ($NO_2$)
Figure 8B:
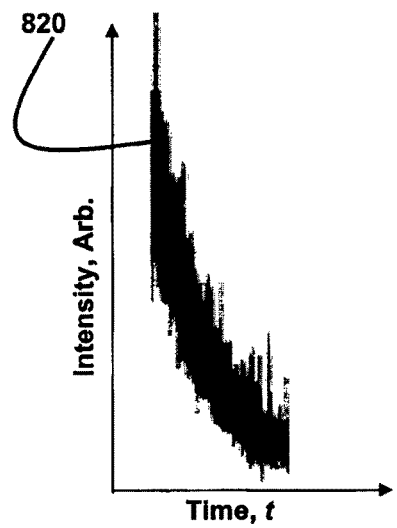

A pulsed $N_2$ laser pumped dye laser with a line width of 0.04 nm firing at about 10 Hz was used as the laser source for a CRDS measurement system. 100 single-shot ring-down waveforms at each interrogated wavelength for both an evacuated cavity (with a pressure P<0.1 Torr) and with $NO_2$ (of initially currently unknown concentration) in the cavity see for example single-shot ring-down waveforms (actually in this case inverted ring-up waveforms) in plots 810 and 820 of FIGS. 8A and 8B respectively. In the particular set-up used, the laser source was not stabilised in either output power or wavelength and mode-matching of the laser source to the cavity was far from optimal, therefore significant noise in the ring-down waveforms was expected and is clearly observed in plots 810 and 820.

In the traditional method of determining spectral data points from the ring-down waveform each individual ring-down waveform was fitted to obtain a value for the time constant $\tau$, and this typically uses a least squares fitting method. Approximately 10% of the decay constants fitter which were more than two standard deviations from the mean were discarded. Due to the noisy laser source, significant variation was observed for shot-to-shot fitting measurements of the time constant $\tau$. Total analysis time for fitting of the data was approximately two hours. A small time advantage would obviously be seen if averaging of a few ring-down waveforms were averaged before the fitting procedure, however, this advantage would be minimal.

The data was also analysed in accordance with the methods described above. In order to place the data in the correct form for the Fourier-based analysis, 20 waveforms were digitally compiled for both the evacuated cavity and the cavity with unknown pressure of $NO_2$ where every second waveform is reversed in time (see plots 815 and 825 of FIG. 9 respectively). To ensure all peaks of the Fourier-transformed data were positive, only the Fourier power spectrum of waveforms 815 and 825 were computed, and the ratio of the amplitudes (magnitude) of the second peak and first peaks in the Fourier-transformed spectrum (ignoring the DC peak at 0 Hz). Enough ring-down data was obtained to generate a Fourier transform (using a fast-Fourier transform in the present example) and analyse 5 waveforms at each wavelengths. The analysis time for this step was less than 5 seconds, therefore clearly making this technique vastly superior to the traditional analysis measurements at least as a function of the time to conduct the analysis phase.

Figure 9:
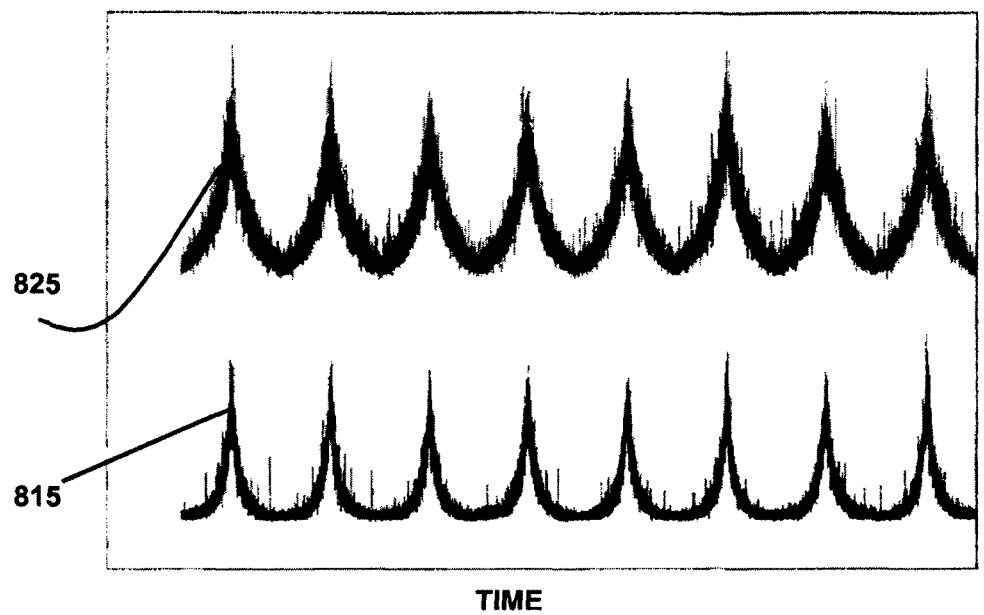
FIG. 9 is a collection of multiple cavity ring-down spectra of the type in FIGS. 8A and 8B compiled for the purpose of performing a Fourier transform analysis as described herein.
Figure 10:
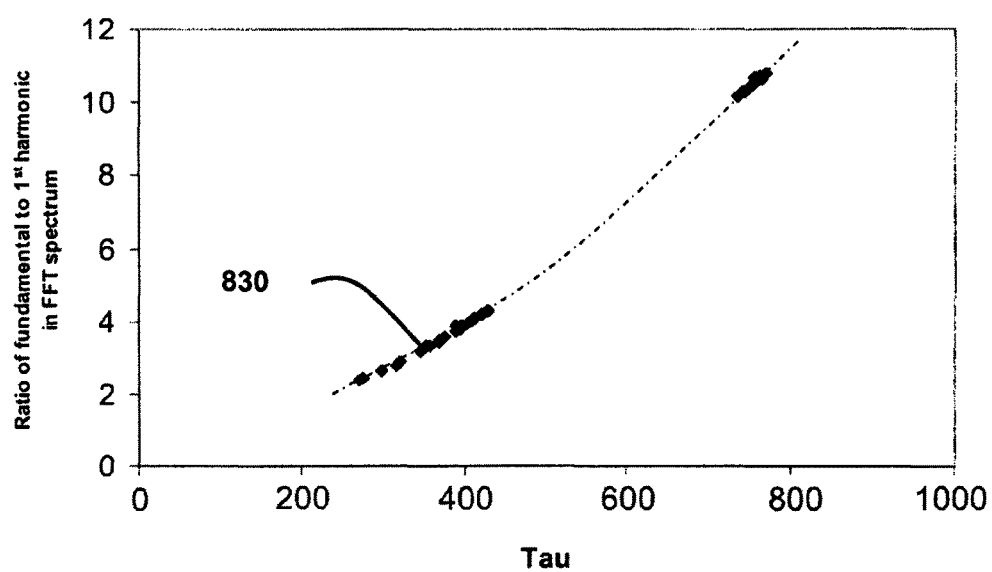
FIG. 10 is a is a plot of the relationship between the observed time-constant and the observed peak ratio between the first and the second peaks in the Fourier-transformed signal of the measured ring-down waveforms with the absorbing species in the CRDS cavity.

FIG. 10 is a plot of the relationship between the observed time-constant $\tau$ and the observed peak ratio between the first and the second peaks in the Fourier-transformed signal of waveform 825 (of FIG. 9). This calibration curve 830 is analogous to the calibration curve of FIG. 4 that has been obtained experimentally. The ring-down decay constant $\tau$ was determined by fitting individual ring-down signal output traces (e.g. 820 of FIG. 8B) to an exponential decay and averaging 200 shots per wavelength using the traditional least squares fitting method for analysing ring-down waveforms. This was then compared to the ratio of the frequency components obtained using the present method to create the calibration curve 830—the ratio on the y-axis of FIG. 10 is simply the ratio between the fundamental and first harmonic peaks in the Fourier-transformed signal (using an Fast Fourier Transform in the present instance) of the waveform 825 of FIG. 9, was obtained by firstly performing the traditional method and comparing this to the ratios of the frequency components obtained using the present method. In practice this calibration curve would be determined for each particular spectrometer as a function of various sampling parameters (eg. sampling time and sampling length) and this calibration data would be stored with the spectrometer and be applied for the analysis of data subsequently taken with the particular spectrometer. As expected, this relationship is quite nonlinear although fitting of this data can be performed to correct for the non-linearity.

Figure 11A:
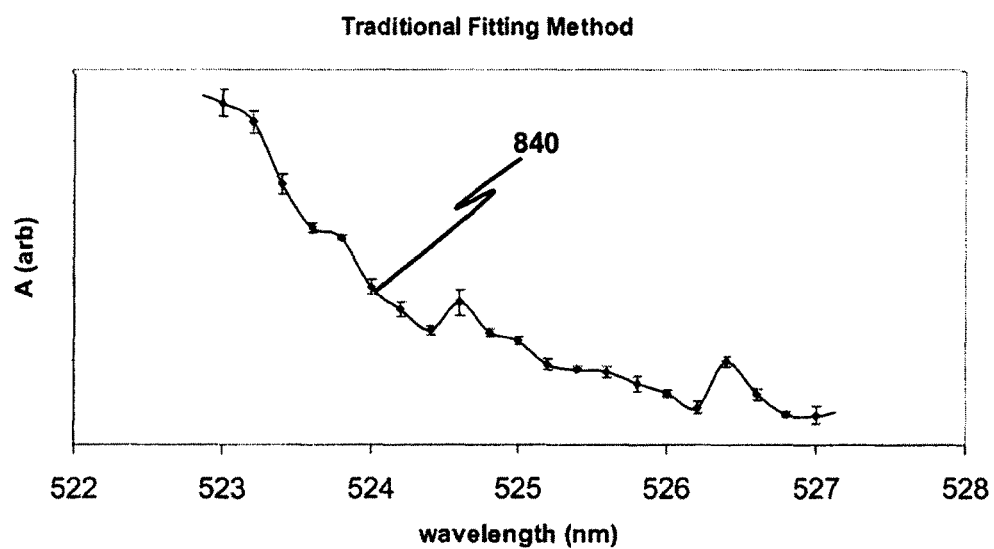
FIG. 11A is a an absorption spectrum (($1/\tau - 1/\tau_o$) vs wavelength) obtained by the traditional method of analysing CRDS ring-down waveforms.
Figure 11B:
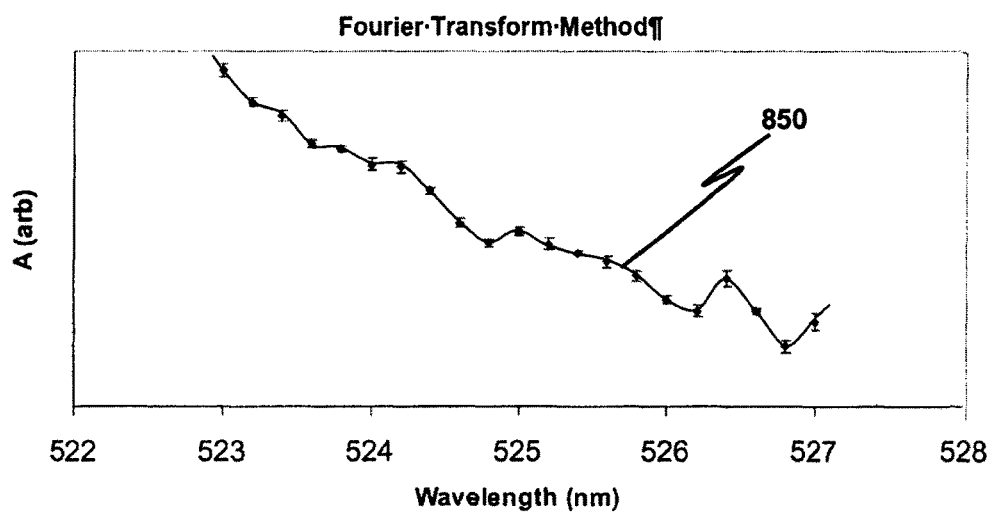
FIG. 11B is a uncorrected absorption spectrum ((ratio ($NO_2$)-ratio(baseline)) vs wavelength) obtained by the Fourier-transform method described herein.

FIGS. 11A and 11B respectively show an absorption spectrum $[(1/\tau-1/\tau_o)$ vs wavelength] 840 obtained by the traditional method where $\tau_o$ is the time constant of the evacuated cavity, and an uncorrected absorption spectrum $[(\text{ratio}(NO_2)-\text{ratio}(\text{baseline}))$ vs wavelength]. The ratio used to determine the uncorrected absorption spectrum 850 using the Fourier-transform method described herein is obtained by taking the ratio of the amplitudes in the power spectrum of the first and second peaks in the Fourier transformed data for both the evacuated cavity [i.e. ratio(baseline)] and the cavity with the unknown concentration of $NO_2$ [i.e. (ratio $(NO_2)$], both as a function of the wavelength of the laser source. In both cases, error bars represent one standard deviation. Lines connecting the data points in each Figure are merely as an aid to the eye. Using only a ratio between the first and second two peaks in the Fourier-transformed signal, the error is each data already smaller than for similar data points in the traditional method. Also note that data has been discarded from the calculation in the traditional method whereas no data has been discarded for calculation of the absorbance spectrum using the Fourier-transform method described herein—all the data collected is used in the calculation. The average standard deviation of each point in the traditional method is about 2% while for the present Fourier-transform method it is only 1.2%. It is expected that significant improvements still will be seen with comparison of the ratios of higher-order components in the Fourier-transformed signal are determined and used in the calculation of the time-constants for each measurement.

As can be seen in FIGS. 11A and 11B the present method provides an analysis technique with superior error handling and significantly reduced time requirements over the traditional methods of signal analysis. Additional gains are expected by implementing the data processing of the present Fourier transform mixing method in hardware, for example field programmable gate arrays (FPGA) which are designed for parallel digital hardware-based processing which is intrinsically faster than performing the computations on a computer and speed gains of at least two or three orders of magnitude are expected. Hardware implementation using FPGAs would also provide a significant advantage in the size of the overall system as the hardware can be designed to perform multiple functions of the systems, for example control of the laser source, generation of the square wave modulation source for modulating the laser source and/or demodulating the detected time-decay signal output into a number of frequency components for ratio analysis, and can also be configured for controlling the locking of the CRDS cavity to the source and performing all the data processing on the detected signal, and controlling all inputs and outputs to the system.

EXAMPLE 2

The digital demodulation method described herein can be employed as an alternate method for analyzing an FTIR interferogram, in the absence of interfering species with sharp overlapping absorption features. The result is a near zero-background measurement eliminating the need for, and noise introduced by, taking a ratio with a background spectrum.

For example, the Fourier transform method disclosed herein, was used to measure the isotope ratios in carbon $^{12}C$ and $^{13}C$ (respectively 98.1% and 1.9% natural abundance) with the ratio defined as $^{13}C/^{12}C$. This ratio can act as a signature and can be used to determine the origin of carbon compounds e.g. petrochemicals, graphite, or alternatively the origin of synthetic materials by the combination of the isotope ratios of different elements. This ratio can also be used, among many others, in biology (eg. determination of the diets of organisms or the origin or growth conditions of plants) or in medicine (eg. to detect the presence of certain bacteria for example typically present in ulcers).

Figure 12:
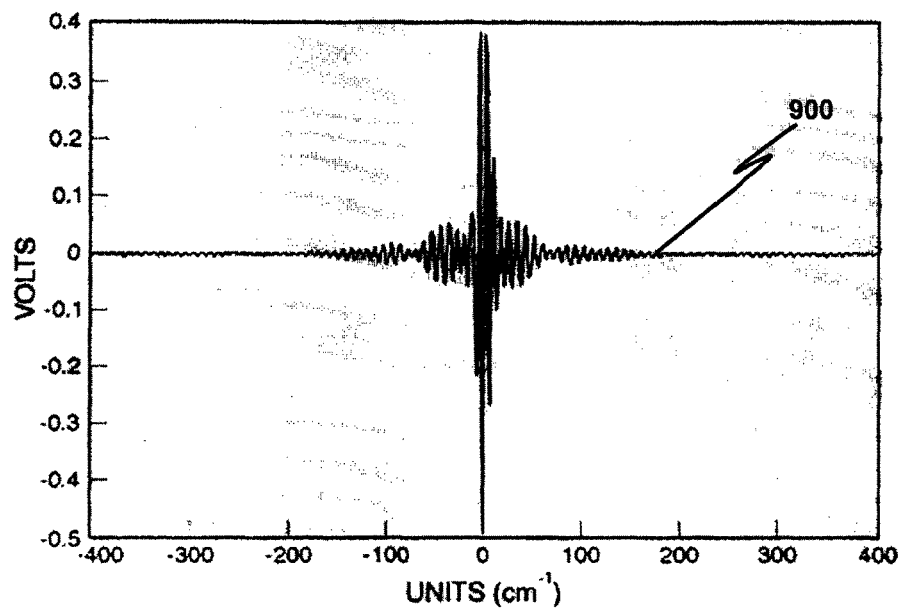
FIG. 12 is a sample interferogram from an FTIR interferometer.

A sample of benzoic acid was quantitatively mixed with $^{13}C$ labelled benzoic acid to control the combination of $^{13}C$ in the sample. 0.20 to 0.40 gram pellets of benzoic acid were combusted in excess oxygen to form $CO_2$. The product CO2 of the combustion was placed in the FTIR spectrometer with a Michelson Interferometer configuration to determine the $^{13}C/^{12}C$ ratio. FIG. 12 shows a sample interferogram 900 obtained from a FTIR spectrometer. The interferogram is symmetrical about the y-axis and is a composition of multiple frequency waves. The centre portion of the interferogram (the "centreburst") is where the distance between the two mirrors in the Michelson interferometer are equal.

Figure 13:
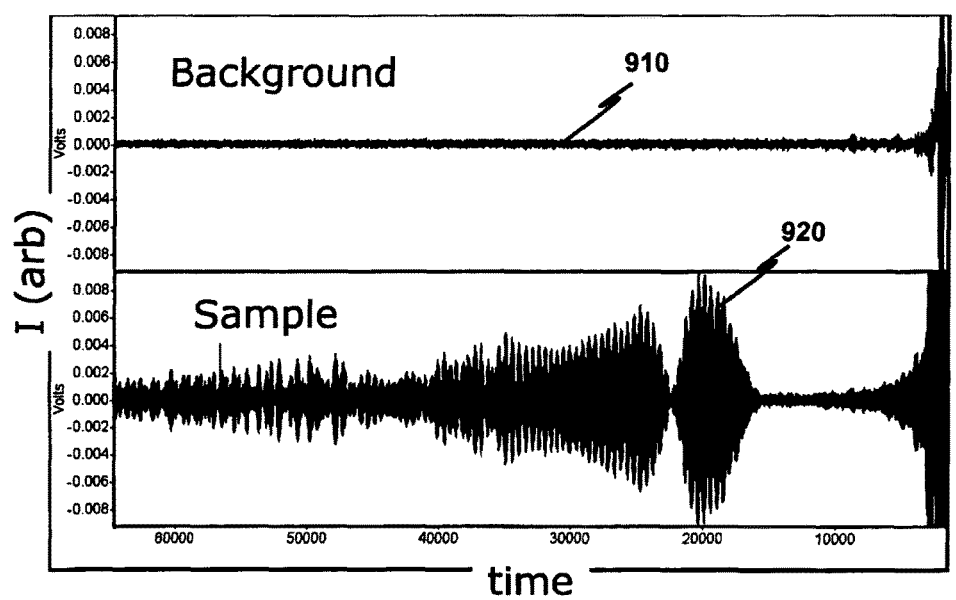
FIG. 13 shows a plot of interferograms from an FTIR interferometer with and without a sample under test.
Figure 14:
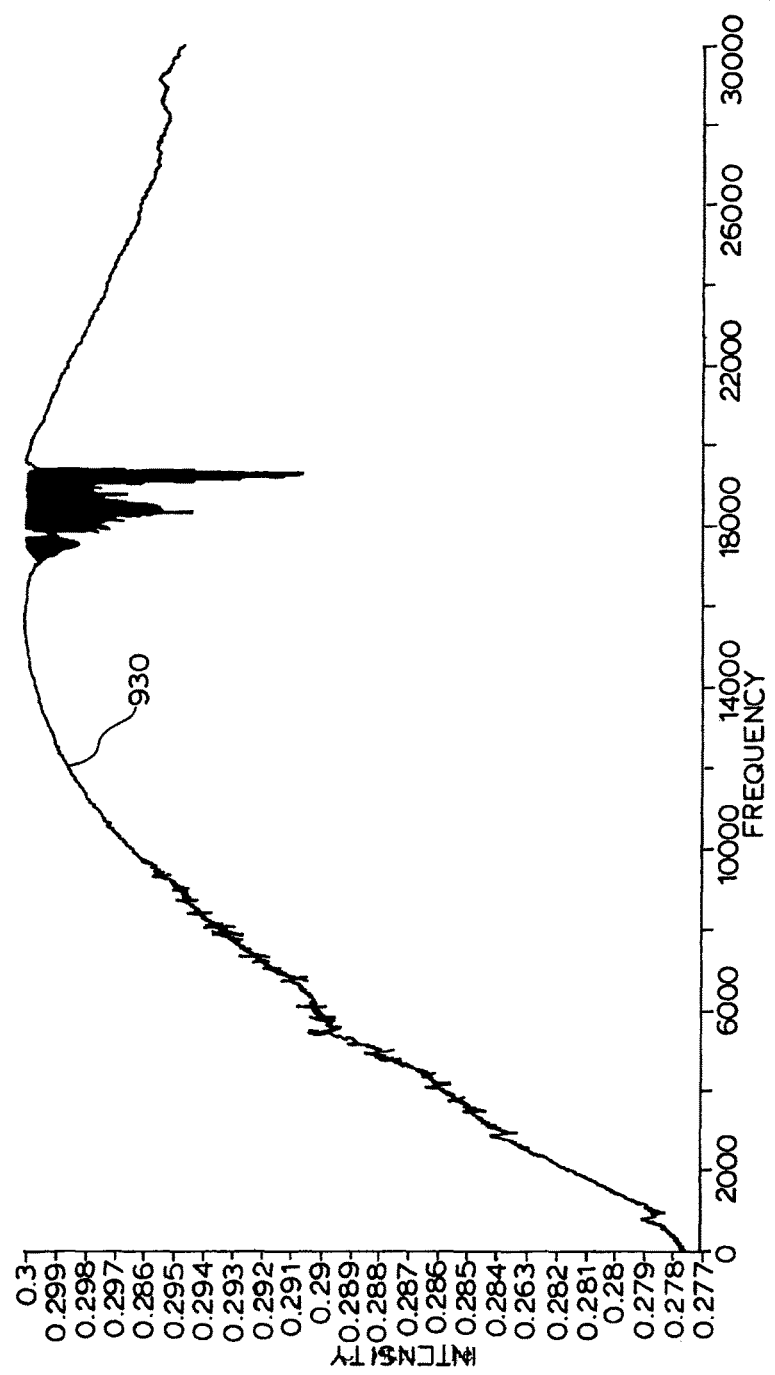
FIG. 14 shows a plot of the Fourier transformed output from the FTIR of the sample interferogram of FIG. 13.
Figure 15:
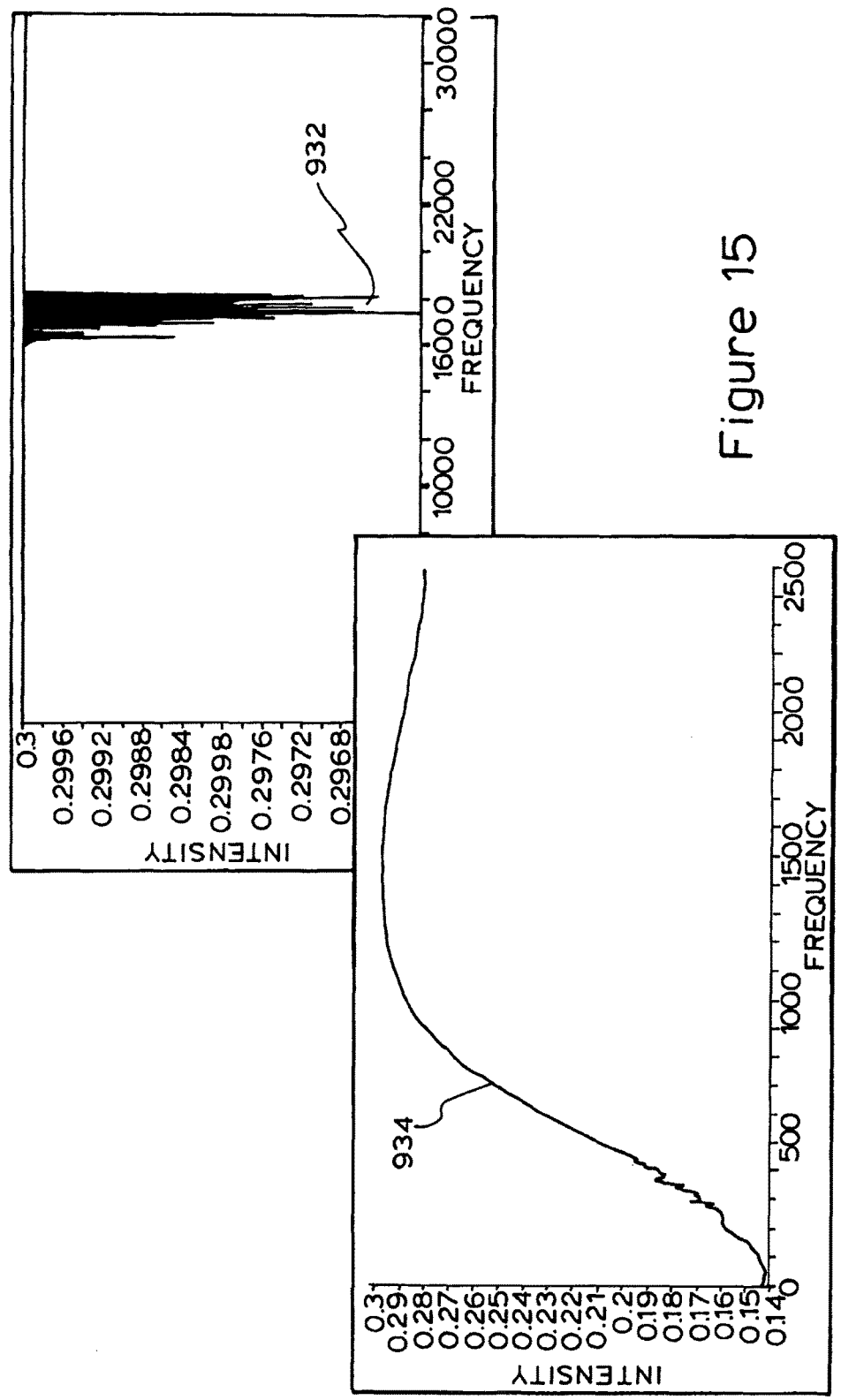
FIG. 15 is the background and signal components of the FTIR output of FIG. 14.

FIG. 13 shows interferogram signals from the FTIR of the background signal 910 with no sample in the spectrometer and also an interferogram 920 of the $CO_2$ sample. The transmission through the sample (1) may be separated from the background signal ($I_o$) by eliminating the centreburst and transforming data at later times (i.e. times above 10,000 in FIG. 13). FIG. 14 shows the FTIR signal output 930, i.e. the Fourier transform of the interferogram 920 (including the centreburst), which comprises the $CO_2$ absorption spectrum (932 of FIG. 15) and the spectral content and intensity of the source (934 of FIG. 15).

Figure 16:
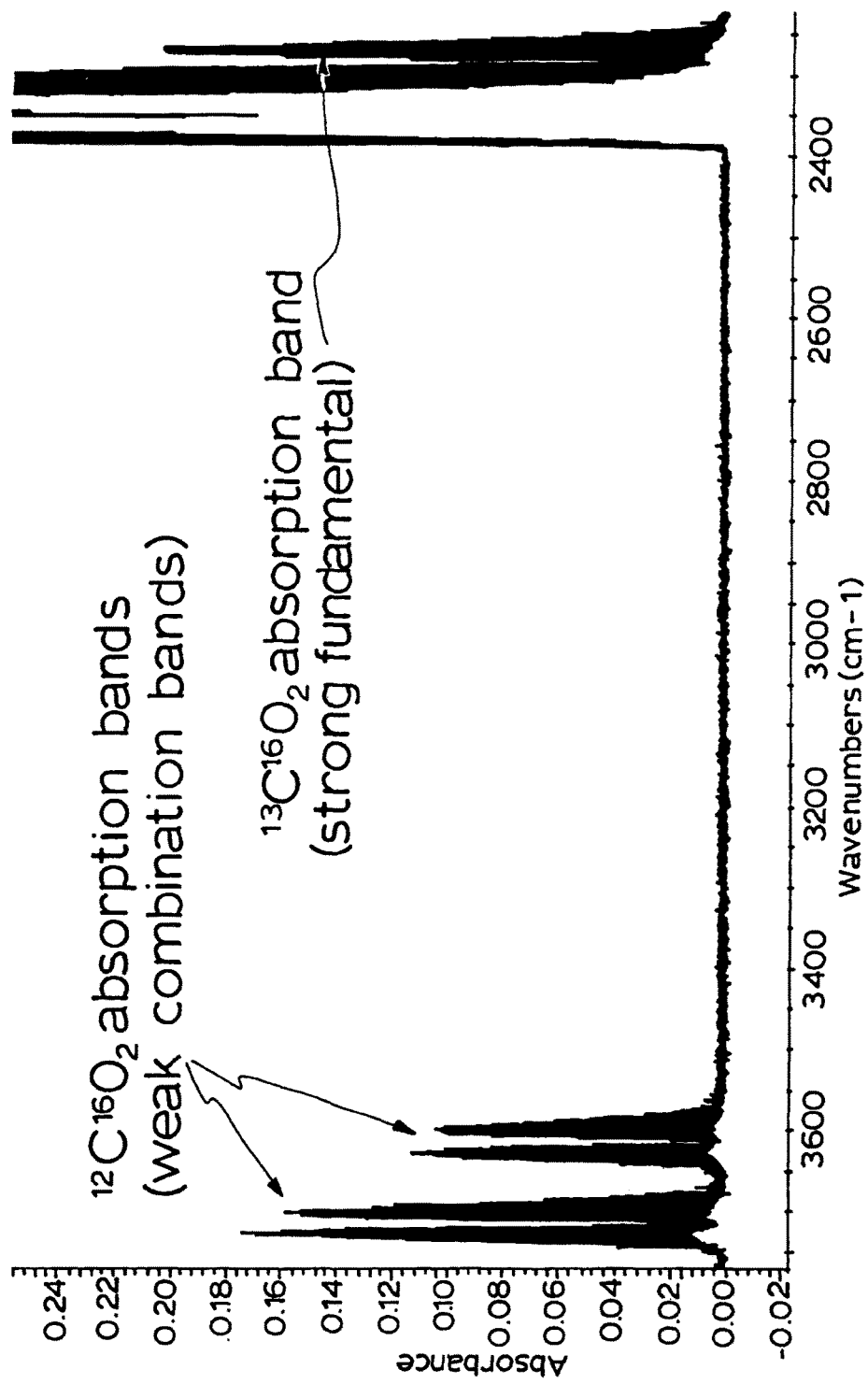
FIG. 16 is an example absorption spectrum of $^{12}C^{16}O_2$ and $^{13}C^{16}O_2$ used as a local oscillator signal in the present methods and systems.

FIG. 16 is an FTIR absorption spectrum of $^{12}C^{16}O_2$ and $^{13}C^{16}O_2$ obtained using the methods and systems disclosed herein which shows a strong fundamental absorption band of $^{13}C^{16}O_2$ around 2300 $cm^{-1}$ and weak combination bands of $^{12}C^{16}O_2$ around 3700 $cm^{-1}$. Comparing fundamental absorption peaks to those in combination bands allow the comparison of peaks of comparable intensity, therefore reducing the impact of limited dynamic range in the system.

As described above with reference to the arrangement of FIG. 7, with an appropriate local oscillator signal the contribution of a set of sine waves to a complex waveform can be determined using a mixer. To extract concentration information directly from an interferogram using a mixer, the appropriate local oscillator signal is a waveform containing a set of sine waves at all frequencies at which absorption occurs. One way to generate this local oscillator signal is to apply an inverse Fourier-transform to an absorption spectrum of the species of interest (i.e. the absorption spectrum of FIG. 16). The resulting interference pattern is then used as the local oscillator and mixed and combined (mixed) with the FTIR interferogram in a mixer to generate a mixed signal—the DC component of the mixer output is a linear function of transmission by the species of interest. This allows the simultaneously monitoring of absorption (absorbance) at many different frequencies.

Figure 17:
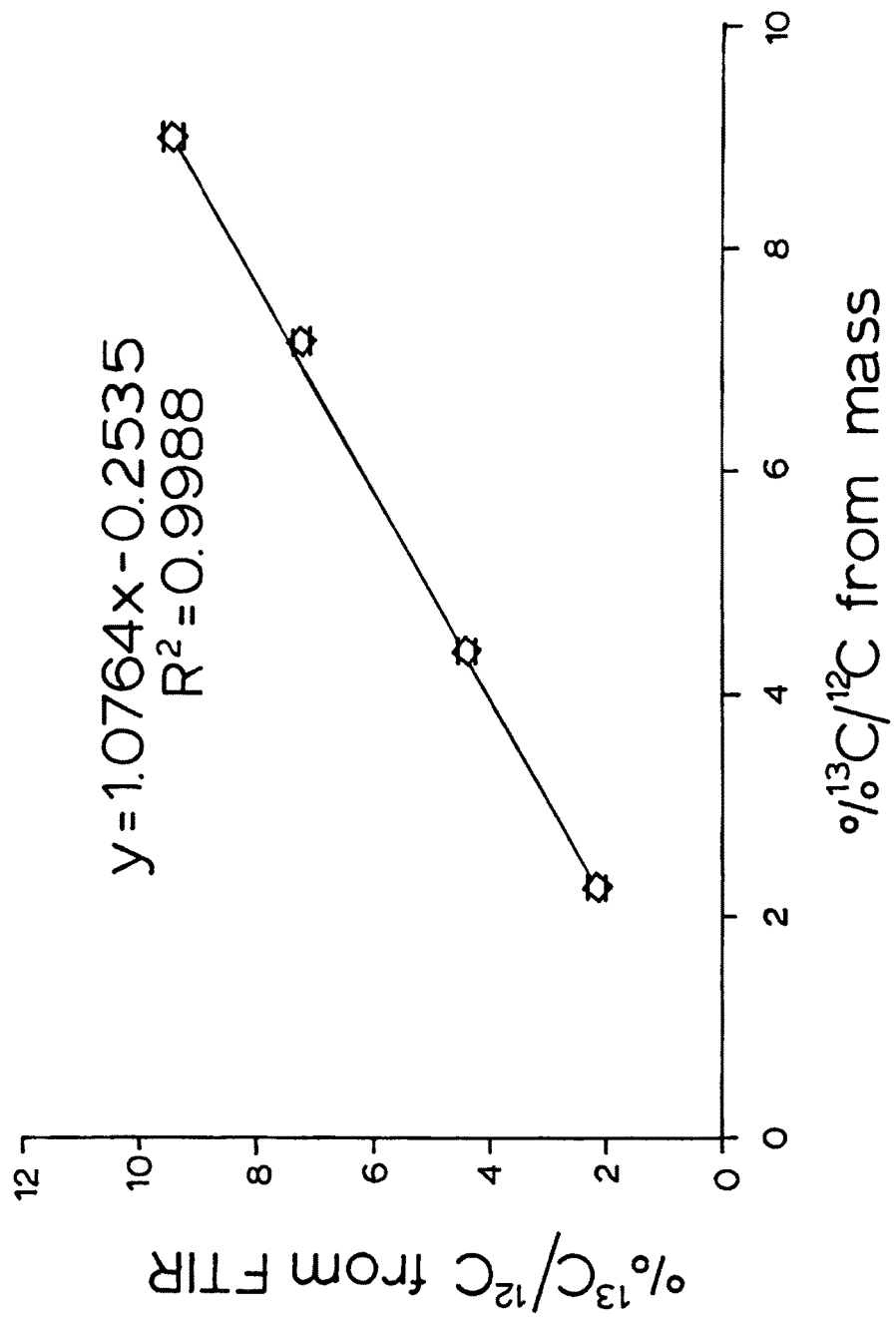
FIG. 17 is plot a comparison between the $^{13}C/^{12}C$ ratio determined using the present methods with that from traditional mass spectrometry methods.

The results of the $^{13}C/^{12}C$ ratio measurement obtained using the FTIR signal and the Fourier transform mixing method disclosed herein using samples with varying $^{13}C$ concentrations are compared with the $^{13}C/^{12}C$ ratio of the samples determined using mass spectrometry. This is shown in FIG. 17. The absolute precision in the present example was limited to about 0.01% due to drifts in the frequency of the absorption features, and this is expected to be improved significantly with use of suitable peak tracking systems. As can be seen, even considering the peak frequency shifts, the agreement of the present method with mass spectrometry measurements is excellent with an $R^2=0.9988$.

This technique has several advantages. First, if data at short mirror displacements is ignored, this technique becomes a near zero background measurement as the only signals which persist to long mirror displacement are those attributable to sharp absorption features. Second, data analysis is fast. With an appropriate local oscillator signal, a digital mixer can be applied to interferograms as fast as or even faster than the signal acquisition process. Finally, as with CRDS systems described above, this approach is insensitive to all noise sources that occur at frequencies other than those in the local oscillator signal generated by the local oscillator.

It will be appreciated that the methods and systems described/illustrated above at least substantially provide improved systems and methods for rapid digital optical spectrum analysis of absorbance data, being particularly useful for real-time spectral monitoring of an absorbance signal, although not limited to this field. For example the methods may also be used for quantification of a modulated optical signal aver being transported over a communications link such as in free-space or optical fibre, whereby the modulated signal degrades from a signal initially resembling a square-wave or quasi-square wave signal to a signal that is more disperse in time and resembles closer to a quasi-triangle wave signal—in this method the analysis of the degradation of the optical signal may be useful for example in determining the quality of the transmission over the communications link and/or the quality of any optical fibre links in the communications link. It will thus be appreciated that the methods and systems provided herein have far-reaching application and are not linked just to the optical domain, but also to signals in other electronic systems, e.g, electronic signals or microwave/shortwave/long-wave/mobile communications among many others and use of the present methods in any such applications is use in the spirit of the invention.

Thus, the systems and methods described herein, and/or shown in the drawings, are presented by way of example only and are not limiting as to the scope of the invention. Unless otherwise specifically stated, individual aspects and components of the signal analysis methods and apparatus may be modified, or may have been substituted therefore known equivalents, or as yet unknown substitutes such as may be developed in the future or such as may be found to be acceptable substitutes in the future. The signal analysis methods and apparatus may also be modified for a variety of applications while remaining within the scope and spirit of the claimed invention, since the range of potential applications is great, and since it is intended that the present signal analysis methods and apparatus be adaptable to many such variations.

REFERENCES (1) Anderson, D. Z.; Frisch, J. C.; and Masser, C. S.; "Mirror reflectometer based on cavity decay time", Applied Optics, 1984, Vol. 23, Issue 8, pp. 1238-1245.
(2) Busch, K. W.; and Busch, M. A., Eds.; "Cavity-Ringdown Spectroscopy. An Ultratrace-Absorption Measurement Technique", American Chemical Society, 1999, Vol. 720, ISBN: 9780841236004.
(3) Romanini, D.; and Lehmann, K. K.; "Ring-down absorption spectroscopy of the very weak HCN overtone bands with six, seven, and eight stretching quanta", Journal of Chemical Physics, 1 Nov. 1993, Vol. 99, Issue 9, pp. 6287-6301.
(4) Spence, T. G.; Harb, C. C.; Paldus, B. A.; Zare, R. N.; Willke, B.; and Byer, R. L.; "A laser-locked cavity ringdown spectrometer employing an analog detection scheme", Review of Scientific Instruments, February 2000, Vol. 71, pp. 347-353.
(5) Leeuwen, N. J. v.; Diettrich, J. C.; and Wilson, A. C.; "Periodically Locked Continuous-Wave Cavity Ringdown Spectroscopy", Applied Optics, 2003, Vol. 42, Issue 18, pp. 3670-3677.
(6) Esler, M. B.; Griffith, D. W. T.; Wilson, S. R.; and Steele, L. P.; "Precision Trace Gas Analysis by FT-IR Spectroscopy. 1. Simultaneous Analysis of CO2, CH4, N2O, and CO in Air", Analytical Chemistry, 2000, Vol. 72, pp. 206-215.
(7) Haaland, D. M.; and Thomas, E. V.; "Partial least-squares methods for spectral analyses. 1. Relation to other quantitative calibration methods and the extraction of qualitative information", Analytical Chemistry, June 1988, Vol. 60, Issue 11, pp. 1193-1202.
(8) Alcott, G. R.; van Mol, T. A. M. B.; and Spee, K. C. I. M. A.; "Evaluation of Chemometric Models in an FTIR Study of the Gas Phase During Atmospheric-Pressure CVD of Tin Oxide Thin Films", Chemical Vapor Deposition, October 2000, Vol. 6, Issue 5, pp. 261-268.
(9) Wabomba, M. J.; and Small, G. W.; "Robust Classifier for the Automated Detection of Ammonia in Heated Plumes by Passive Fourier Transform Infrared Spectrometry", Analytical Chemistry, 2003, Vol. 75, Issue 9, pp. 2018-2026.
(10) Monfre, S. L.; and Brown, S. D.; "Quantitative Fourier-Domain Analysis. Part I: Analysis of Raw FT-IR Interferograms", Applied Spectroscopy, November 1992, Vol. 46, Issue 11, pp. 1699-1710.
(11) Espinoza, Luis H.; Niemczyk, Thomas M.; and Stallard, Brian R.; "Generation of Synthetic Background Spectra by Filtering the Sample Interferogram in FT-IR", Applied Spectroscopy, 1998, Vol. 53, Issue 3, pp. 375-379.
(12) Rothman, L. S.; Rinsland, C. P.; Goldman, A.; Massie, S. T.; Edwards, D. P.; Flaud, J.-M.; Perrin, A.; Camy-Peyret, C.; Dana, V.; Mandin, J.-Y.; Schroeder, J.; McCann, A.; Gamache, R. R.; Wattson, R. B.; Yoshino, K.; Chance, K. V.; Jucks, K. W.; Brown, L. R.; Nemtchinov, V.; Varanasi, P.; "The HITRAN molecular spectroscopic database and HAWKS (HITRAN Atmospheric Workstation): 1996 edition", Journal of Quantitative Spectroscopy and Radiative Transfer, November 1998, Vol. 60, Issue 5, pp. 665-710.
(13) Harris, F. J.; "On the use of windows for harmonic analysis with the discrete Fourier transform", Proceedings of the IEEE, January 1978, Vol. 66, Issue 1, pp. 51-83.

The invention claimed is:

1. A method for determining a decay of an optical beam passing through a sample, said method comprising:
detecting, by an optical detector, the optical beam passing through the sample;
converting, by the optical detector, the detected optical beam into a time-domain signal;
mixing, in a mixer, the time-domain signal with a local oscillator signal generated by a local oscillator, the local oscillator signal comprising two or more sinusoidal waves, wherein the mixing generates a set of Fourier transformed time-domain signals corresponding to the two or more sinusoidal waves of the local oscillator signal;
determining the magnitude of each of the Fourier transformed time-domain signals;
determining a ratio of the magnitude of at least two Fourier transformed time-domain signals from the set of Fourier transformed time-domain signals, wherein the at least two Fourier transformed time-domain signals correspond to different frequencies;
determining a decay constant of the time-domain signal based on the determined ratio, wherein the decay constant is a rate of decay over time; and
determining the decay of the optical beam based on the determined decay constant.

2. The method as claimed in claim 1, wherein the two or more sinusoidal waves comprises a first sinusoidal wave at a fundamental frequency and second sinusoidal waves at harmonic frequencies of the fundamental frequency.

3. The method as claimed in claim 1, wherein the local oscillator signal is a square wave, the square wave comprising the two or more sinusoidal waves.

4. The method as claimed in claim 1, wherein the local oscillator signal is a complex waveform comprising the two or more sinusoidal waves.

5. The method as claimed in claim 1, wherein the optical beam is an absorbance signal.

6. The method as claimed in claim 1, wherein the optical beam is a cavity-ring down signal.

7. The method of claim 6, wherein the optical beam is generated by an excitation source selected from the group consisting of:
a continuous wave source,
a quasi-continuous wave source,
a pulsed source, and
a modulated source.

8. The method of claim 7, wherein the excitation source is a laser source.

9. The method of claim 1, wherein the optical beam is an interferogram signal.

10. The method of claim 1, further comprising:
generating, by a modulator, a modulation signal and the local oscillator signal;
modulating an excitation source using the modulation signal;
resonating, in an optical cavity, modulated light from the excitation source; and
outputting, from the optical cavity, the optical beam,
wherein the decay of the optical beam corresponds to an absorbance of a sample.

11. The method of claim 10, wherein the optical cavity is adapted to accept the sample so that, in use, the sample absorbs at least a portion of the resonating light.

12. The method of claim 1, wherein the sample is disposed between reflectors, which form an optical cavity where the optical beam resonates in the optical cavity.

13. The method of claim 12, wherein the reflectors each have a reflectivity at a wavelength of the optical beam.

14. A system for determining a decay of an optical beam passing through a sample, the system comprising:
- a detector for detecting the optical beam passing through the sample, and converting the detected optical beam into a time-domain signal;
- a mixer for mixing the time-domain signal with a local oscillator signal, the local oscillator signal comprising two or more sinusoidal waves, and generating a set of Fourier transformed time-domain signals corresponding to the two or more sinusoidal waves of the local oscillator signal; and
- a determiner for determining the magnitude of each of the Fourier transformed time-domain signals, determining a ratio of the magnitude of at least two Fourier transformed time-domain signals from the set of Fourier transformed time-domain signals, wherein the at least two Fourier transformed time-domain signals correspond to different frequencies, determining a decay constant of the time-domain signal based on the determined ratio, wherein the decay constant is a rate of decay over time, and determining the decay of the optical beam based on the determined decay constant.

15. The system as claimed in claim 14, wherein the optical beam is an interferogram signal.

16. The system as claimed in claim 14, further comprising:
- a modulator for generating a modulation signal and the local oscillator signal;
- an excitation source adapted to be modulated using the modulation signal; and
- an optical cavity adapted to resonate modulated light from the excitation source and to output the optical beam;
- wherein the decay of the optical beam corresponds to an absorbance of a sample.

17. The system as claimed in claim 16, wherein:
- the optical cavity is adapted to accept the sample so that, in use, the sample absorbs at least a portion of the resonating light.

18. The system as claimed in claim 14, wherein the optical beam is an absorbance signal.

19. The system as claimed in claim 14, wherein the optical beam is a cavity-ring down signal.

20. The system as claimed in claim 19, further comprising an excitation source selected from the group consisting of:
- a continuous wave source,
- a quasi-continuous wave source,
- a pulsed source, and
- a modulated source.

21. The system as claimed in claim 20, wherein the excitation source is a laser source.

22. The system as claimed in claim 14, wherein the system is adapted for analysing the time-domain signal in real time.

23. The system of claim 14, where the two or more sinusoidal waves comprises a first sinusoidal wave at a fundamental frequency and second sinusoidal waves at harmonic frequencies of the fundamental frequency.

24. The system of claim 14, wherein the local oscillator signal is a square wave, the square wave comprising the two or more sinusoidal waves.

25. The system of claim 14, wherein the local oscillator signal is a complex waveform comprising the two or more sinusoidal waves.

26. The system of claim 14, further comprising:
- a pair of reflectors forming an optical cavity, each reflector have a reflectivity at a wavelength of the optical beam; and
- the sample in the optical cavity.

* * * * *